United States Patent [19]
Junichi et al.

[11] Patent Number: 6,020,317
[45] Date of Patent: Feb. 1, 2000

[54] GLYCEROL DERIVATIVE, DEVICE AND PHARMACEUTICAL COMPOSITION

[75] Inventors: Yano Junichi, Nara; Tadaaki Ohgi, Otsu, both of Japan

[73] Assignee: Nippon Shinyaku Co. Ltd., Kyoto, Japan

[21] Appl. No.: 08/507,518

[22] PCT Filed: Feb. 17, 1994

[86] PCT No.: PCT/JP94/00237

§ 371 Date: Oct. 23, 1995

§ 102(e) Date: Oct. 23, 1995

[87] PCT Pub. No.: WO94/19314

PCT Pub. Date: Sep. 1, 1994

[30] Foreign Application Priority Data

Feb. 19, 1993 [JP] Japan .................................. 5-054939

[51] Int. Cl.⁷ .................................................. A61K 31/70
[52] U.S. Cl. ............................ 514/44; 514/476; 514/599; 514/602
[58] Field of Search ................................ 554/227; 514/44, 514/476, 599, 601

[56] References Cited

U.S. PATENT DOCUMENTS 4,851,232  7/1989  Urquhart et al. .
4,853,229  8/1989  Theeuwes .
4,961,932  10/1990  Theeuwes .
5,030,454  7/1991  Theeuwes .
5,252,706  9/1993  Kitaguchi et al. .

FOREIGN PATENT DOCUMENTS 146258    6/1985   European Pat. Off. .
451763   10/1991   European Pat. Off. .
WO85/2118  5/1985  WIPO .

*Primary Examiner*—Deborah Carr
*Attorney, Agent, or Firm*—Graham & James LLP

[57] ABSTRACT

The object of the invention is to provide a lipid device functionally equivalent to the so-called cationic liposome and of lesser toxicity and a lipid or the like as a component of the device.

The compound of the invention includes but is not limited to 3-O-(4-dimethylaminobutanoyl)-1,2-O-dioleylglycerol, 3-O-(2-dimethylaminoethyl)carbamoyl-1,2-O-dioleylglycerol, 3-O-(2-diethylaminoethyl) carbamoyl-1,2-O-dioleylglycerol and 2-O-(2-diethylaminoethyl) carbamoyl-1,3-O-dioleoylglycerol. The device of the invention comprises such a lipid and a phospholipid.

By administering a double-stranded RNA, for instance, together with the device of the invention, the double-stranded RNA can be safely delivered to the site of action.

12 Claims, No Drawings

GLYCEROL DERIVATIVE, DEVICE AND PHARMACEUTICAL COMPOSITION

TECHNICAL FIELD

The present invention relates to compounds of the following general formula [I].

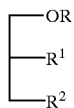

wherein $R^1$ and $R^2$ are not the same and each represents OY or —A—$(CH_2)$n-E. n represents a whole number of 0–4. E represents pyrrolidino, piperidino, substituted or unsubstituted piperazino, morpholino, substituted or unsubstituted guanidino, or

(where $R^3$ and $R^4$ are the same or different and each represents hydrogen, lower($C_{1-4}$)alkyl, hydroxy-lower($C_{1-4}$) alkyl, or mono- or di- (lower)alkylamino-alkyl($C_{2-6}$)).

A represents the following ①, ②, ③, ④, ⑤, ⑥, or ⑦.

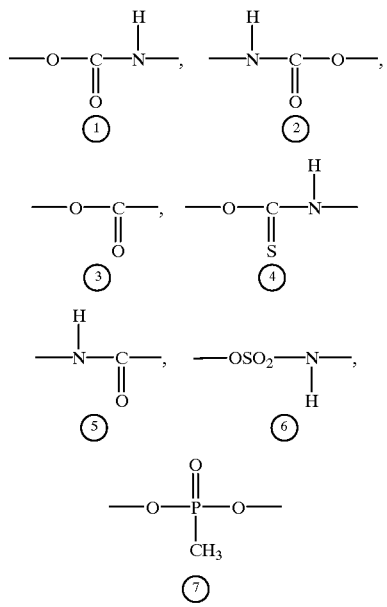

R and Y are the same or different and each represents a saturated or unsaturated aliphatic hydrocarbon group of 10–30 carbon atoms or a saturated or unsaturated fatty acid residue of 10–30 carbon atoms.

The compound according to the present invention (hereinafter referred to as the compound of the invention) is of great use as a component of the DDS (drug delivery system) device. The term 'device' means a material having the function of transporting a physiologically active substance, e.g. a carrier.

BACKGROUND ART

It is known that a device comprising a certain positively charged lipid (for example, a cationic liposome) is useful for the transfer of genes into the cell (e.g. JP-A-4108391, WO91/17424). It is also known that when a nucleic acid such as a double-stranded RNA is administered together with a device such as a cationic liposome, a potentiated interferon inducer action is realized (U.S. Pat. No. 5,049,386). It is generally conjectured that since the nucleic acid of, for example, a gene is negatively charged, it forms a complex with a cationic liposome and the complex becomes fused to the cell membrane and the nucleic acid of the gene or the like finds its way into the cell.

As said cationic liposome, Lipofectin (trademark, Bethesda Research Laboratories Life Technologies Inc.) comprising N-[1-(2,3-dioleyloxy)propyl]-N,N,N-trimethylammonium chloride (hereinafter referred to as DOTMA) and dioleoylphosphatidylethanolamine in a ratio of 1:1 is well known.

However, because DOTMA as a component of Lipofectin is a quaternary ammonium compound and, therefore, has high hemolytic toxicity, it is not suitable for pharmaceutical use.

An attempt has been made to enhance the effect of the liposome by replacing the DOTMA of Lipofectin with a cholesterol derivative (Third International Symposium on Catalytic RNAs and Targeted Gene Therapy for the Treatment of HIV Infection, Dec. 6–11, 1992).

DISCLOSURE OF INVENTION

The object of the present invention is to provide a lipid device which is functionally equivalent to the cationic liposome and, yet, is less toxic and a lipid as a component of the device.

In the course of intensive research, the inventors of the present invention discovered that the above-mentioned problems could be solved by using the compound of the invention in lieu of DOTMA in Lipofectin and have completed the present invention.

One of the essential feature of the present invention resides in the structure of the compound of general formula [I]. The compound of the present invention is a novel compound not described in the literature.

The compound of the present invention is structurally characterized in that where glycerol is the fundamental skeleton, one of the hydroxyl groups of glycerol has been substituted by a group formula —A—$(CH_2)$n-E, where A, n and E are as defined hereinbefore.

Another essential feature of the present invention resides in that A in the above formula —A—$(CH_2)$n-E is the following ①, ②, ③, ④, ⑤, ⑥ or ⑦.

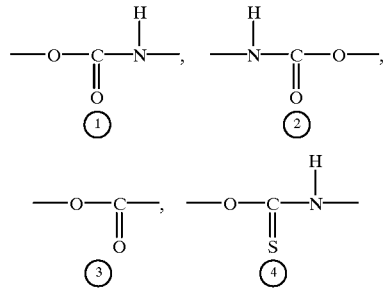

-continued

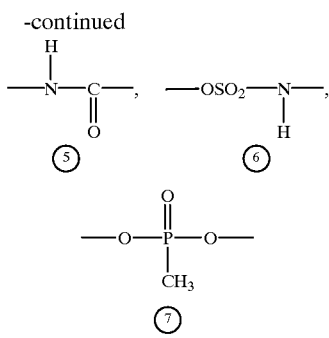

Among specific compounds of the present invention, none have the amine in the substituent group E in the quaternary ammonium form. It is described in JP-A-4108391 that a lipid having a quaternary ammonium group is satisfactory as a lipid constituent of a liposome or device, but such quaternary ammonium compounds are unsuitable for the purpose of the present invention.

The substituted piperazino for E includes 4-methylpiperazino, 4-ethylpiperazino, 4-n-propylpiperazino, 4-isopropylpiperazino, 4-n-butylpiperazino, 4-isobutylpiperazino, 4-(2-hydroxyethyl) piperazino, 4-(2-hydroxypropyl)piperazino, and 4-(3-hydroxypropyl)piperazino, among others.

The substituted guanidino for E includes methylguanidino, ethylguanidino, n-propylguanidino, N,N-dimethylguanidino, N,N-diethylguanidino, N,N-di-n-propylguanidino, N,N'-dimethylguanidino, N,N'-diethylguanidino, N,N'-di-n-propylguanidino, N,N,N'-trimethylguanidino, N,N,N'-triethylguanidino, N,N,N'-tri-n-propylguanidino, N,N,N',N'-tetramethylguanidino, N,N,N', N'-tetraethylguanidino, and N,N,N',N'-tetra-n-propylguanidino, among others.

The lower alkyl for $R^3$, $R^4$ includes methyl, ethyl, n-propyl, isopropyl, n-butyl, isobutyl, sec-butyl, and tert-butyl, among others.

The hydroxy(lower)alkyl for $R^3$, $R^4$ includes hydroxymethyl, 1-hydroxyethyl, 2-hydroxyethyl, 1-hydroxypropyl, 2-hydroxypropyl, and 3-hydroxypropyl, among others.

The mono- or di-(lower)alkylaminoalkyl for $R^3$, $R^4$ includes methylaminomethyl, dimethylaminomethyl, 2-(methylamino)ethyl, 2-dimethylaminoethyl, 3-(methylamino)propyl, 3-dimethylaminopropyl, ethylaminomethyl, diethylaminomethyl, 2-(ethylamino) ethyl, 2-diethylaminoethyl, 3-(ethylamino)propyl, 3-diethylaminopropyl, n-propylaminomethyl, di-n-propylaminomethyl, 2-(n-propylamino)ethyl, 2-(di-n-propylamino)ethyl, 3-(n-propylamino) propyl, and 3-(di-n-propylamino)propyl, among others.

Referring further to general formula [I], R and Y are the same or different and each represents a saturated or unsaturated aliphatic hydrocarbon group of 10–30 carbon atoms or a saturated or unsaturated fatty acid residue of 10–30 carbon atoms as mentioned above. However, the preferred is the case in which R and Y are the same and each represents an unsaturated aliphatic hydrocarbon or unsaturated fatty acid residue of about 12–20 carbon atoms. The most preferred is the case in which both R and Y represent oleyl or oleoyl, for instance.

A is preferably a carbamate bond or an ester bond.

The compound of the present invention has only a very low toxic potential.

The compound of general formula [I] according to the present invention can be obtained by, inter alia, the following processes.

(1) Where $R^1$ represents OY and A represents —O—C (=O)—NH—

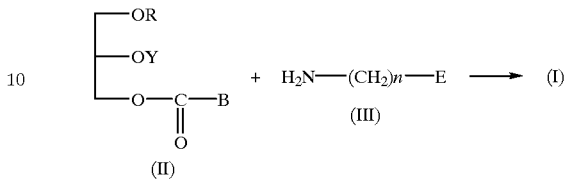

(wherein B is typically imidazolyl, halogen or phenoxy. The halogen may for example be chlorine, bromine or iodine. R, Y, E and n are as defined hereinbefore).

As shown schematically above, compound [I] of the invention can be synthesized by reacting [II] with [III].

This reaction between [II] and [III] can be carried out using 1–3 equivalents of [III] per equivalent of [II] in the presence of a solvent at 0° C.–150° C. for 1–20 hours. The reaction solvent that can be used includes dimethylformamide, pyridine, toluene, benzene, ether, dioxane, tetrahydrofuran, chloroform and so on. To hasten the reaction, a base such as triethylamine can be added. Moreover, [III] may be first converted to a metal salt using sodium hydride, n-butyllithium or the like in the above-mentioned solvent and, then, reacted with [II].

(2) Where $R^1$ represents OY and A represents —NH—C (=O)—O—

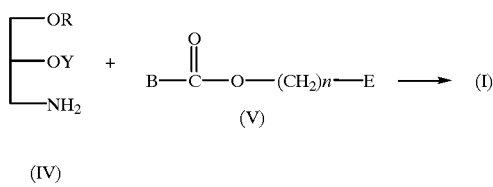

(wherein B, R, Y, E and n are as defined hereinbefore).

Compound [I] of the invention can be synthesized by reacting [IV] with [V] according to the above reaction schema, using reaction conditions similar to those mentioned under (1).

(3) Where $R^1$ represents OY and A represents —NH—C (=O)—O—

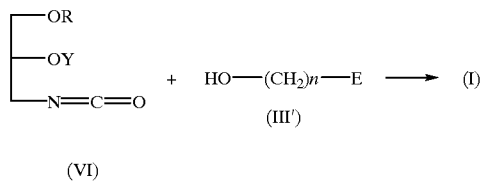

(wherein R, Y, E and n are as defined hereinbefore).

Compound [I] of the invention can be synthesized by reacting [VI] with [III'] as shown schematically above, using reaction conditions similar to those mentioned under (1).

(4) Where $R^1$ represents OY and A represents —O—C (=O)—NH—

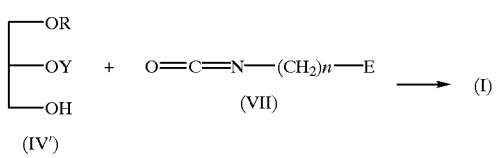

(wherein R, Y, E and n are as defined hereinbefore).

Compound [I] of the invention can be synthesized by reacting [IV'] with [VII] as shown schematically above, using reaction conditions similar to those mentioned under (1).

(5) Where $R^1$ represents OY and $R^2$ represents —A—$(CH_2)$n-E

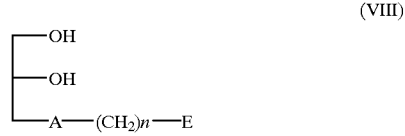

(wherein A, E and n are as defined hereinbefore).

Compound [I] of the invention can be synthesized by transforming the hydroxyl groups of the above compound into the substituent groups R and Y through reaction with suitable acylating agents (e.g. the anhydrides or acid chlorides of fatty acids). This route of synthesis is preferred where R and Y are fatty acid residues.

<Synthesis of the Starting Compounds [IV], [IV'], [V], [VI], [VII], and [VIII]>

(1) Synthesis of Starting Compound [IV']

The starting compound [IV'] can be synthesized typically in accordance with the following reaction schema.

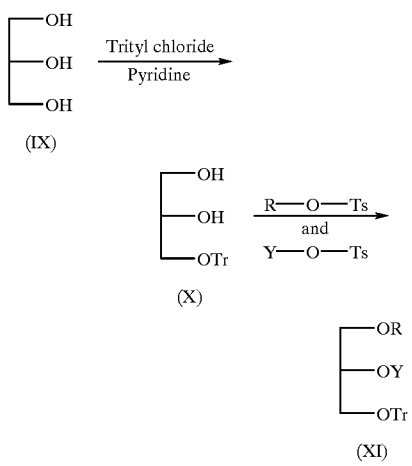

(wherein Tr represents trityl, Ts represents tosyl; R and Y are as defined hereinbefore).

(2) Synthesis of Starting Compound [IV]

The starting compound [IV] can be synthesized typically by the following exemplary process.

Starting with compound [IV'], the compound [IV] can be synthesized by the conventional procedure, e.g. azidation and subsequent reduction.

(3) Synthesis of Starting Compound [v]

The starting compound [V] wherein B is imidazolyl, for instance, can be synthesized by reacting compound [III'] with N,N'-carbonyldiimidazole in pyridine at ambient temperature.

(4) Synthesis of Starting Compound [VI]

The starting compound [VI] can be synthesized by reacting compound [IV] with diphosgene.

(5) Synthesis of Starting Compound [VII]

The starting compound [VII] can be easily synthesized typically by reacting compound [III] with diphosgene or by reacting a compound of the formula HOOC—$(CH_2)$n-E (where n and E are as defined hereinbefore) with DPPA (diphenylphosphoryl azide) in the presence of a tertiary amine such as triethylamine at 0–150° C. and further in the presence of a tertiary amine such as pyridine at 0–150° C.

(6) Synthesis of Starting Compound [VIII]

① The compound [VIII] wherein A represents —O—C(=O)—NH— can be synthesized typically according to the following reaction schema.

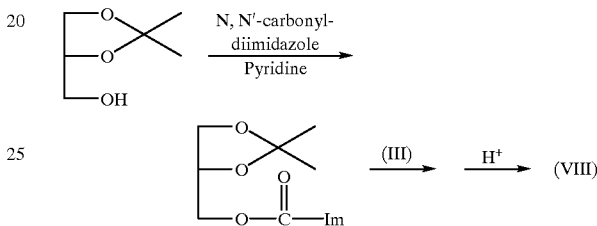

(wherein Im represents imidazolyl)

② The compound [VIII] wherein A represents —NH—C(=O)—O— can be synthesized typically according to the following reaction schema.

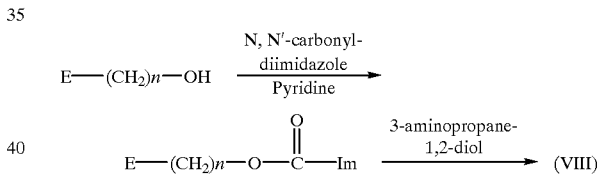

(wherein Im represents imidazolyl; E and n are as defined hereinbefore)

③ The compound [VIII] wherein A represents —O—C(=O)— can be synthesized typically according to the following reaction schema.

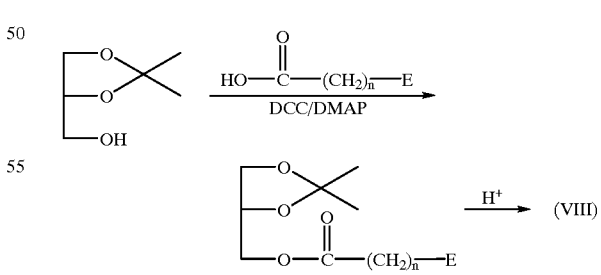

(wherein DCC means dicyclohexylcarbodiimide and DMAP means 4-N,N-dimethylaminopyridine; E and n are as defined hereinbefore)

④ The compound [VIII] wherein A represents —O—C(=S)—NH— can be synthesized typically according to the following reaction schema.

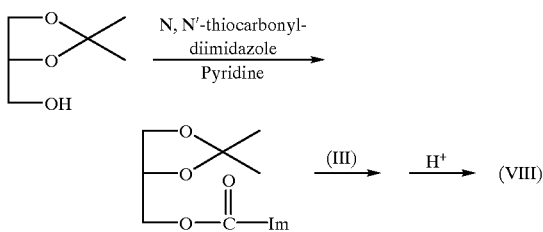

(wherein Im represents imidazolyl)

(5) The compound [VIII] wherein A represents —NH—C(=O)— can be synthesized typically according to the following reaction schema.

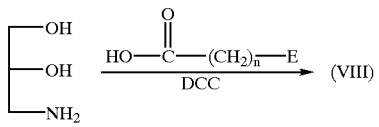

(wherein DCC means dicyclohexylcarbodiimide; E and n are as defined hereinbefore)

(6) The compound [VIII] wherein A represents —OSO$_2$—NH— can be synthesized typically according to the following reaction schema.

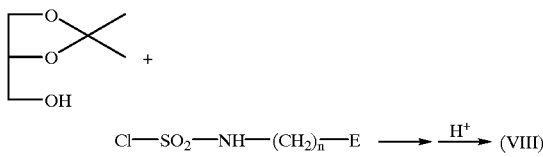

(wherein E and n are as defined hereinbefore)

(7) The compound [VIII] wherein A represents —O—P(=O)(—CH$_3$)—O— can be synthesized typically according to the following reaction schema.

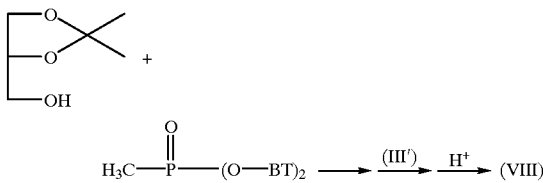

(wherein BT means 1-benzotriazolyl)

The following is a partial list of the compounds of the present invention.

3-O-(2-Dimethylaminoethyl)carbamoyl-1,2-O-dilaurylglycerol,
3-O-(2-Dimethylaminoethyl)carbamoyl-1,2-O-dimyristylglycerol,
3-O-(2-Dimethylaminoethyl)carbamoyl-1,2-O-dipalmitylglycerol,
3-O-(2-Dimethylaminoethyl)carbamoyl-1,2-O-dioleylglycerol,
3-O-(2-Dimethylaminoethyl)carbamoyl-1,2-O-dilinoleylglycerole,
3-O-(2-Dimethylaminoethyl)carbamoyl-2-O-lauryl-1-O-myristylglycerol,
3-O-(2-Dimethylaminoethyl)carbamoyl-1-O-oleyl-2-O-palmitylglycerol,
3-O-(2-Dimethylaminoethyl)carbamoyl-1-O-linoleyl-2-O-oleylglycerol,
3-O-(Dimethylaminomethyl)carbamoyl-1,2-O-dioleylglycerol,
3-O-(3-Dimethylaminopropyl)carbamoyl-1,2-O-dioleylglycerol,
3-O-(4-Dimethylaminobutyl)carbamoyl-1,2-O-dioleylglycerol,
3-O-(2-Diethylaminoethyl)carbamoyl-1,2-O-dioleylglycerol,
3-O-(3-Diethylaminopropyl)carbamoyl-1,2-O-dioleylglycerol,
3-O-(2-Di-n-propylaminoethyl)carbamoyl-1,2-O-dioleylglycerol,
3-O-(2-Diisopropylaminoethyl)carbamoyl-1,2-O-dioleylglycerol,
3-O-(2-Di-n-butylaminoethyl)carbamoyl-1,2-O-dioleylglycerol,
3-O-(2-Diisobutylaminoethyl)carbamoyl-1,2-O-dioleylglycerol,
3-O-(2-Di-sec-butylaminoethyl)carbamoyl-1,2-O-dioleylglycerol,
3-O-[2-(N-Ethyl-N-methylamino)ethyl]carbamoyl-1,2-O-dioleylglycerol,
3-O-(2-Methylaminoethyl)carbamoyl-1,2-O-dioleylglycerol,
3-O-(2-Ethylaminoethyl)carbamoyl-1,2-O-dioleylglycerol,
3-O-(2-n-Propylaminoethyl)carbamoyl-1,2-O-dioleylglycerol,
3-O-(2-n-Butylaminoethyl)carbamoyl-1,2-O-dioleylglycerol,
3-O-(2-Aminoethyl)carbamoyl-1,2-O-dioleylglycerol,
3-O-[2-(N-Methyl-N-(2-hydroxyethyl)amino)ethyl]carbamoyl-1,2-O-dioleylglycerol,
3-O-[2-(N-Ethyl-N-(2-hydroxyethyl)amino)ethyl]carbamoyl-1,2-O-dioleylglycerol,
3-O-[2-(N,N-Di-(2-hydroxyethyl)amino)ethyl]carbamoyl-1,2-O-dioleylglycerol,
3-O-[2-(N-(2-Diethylamino)ethyl-N-methylamino)ethyl]carbamoyl-1,2-O-dioleylglycerol,
3-O-[2-(4-Methylpiperazino)ethyl]carbamoyl-1,2-O-dioleylglycerol,
3-O-(2-Morpholinoethyl)carbamoyl-1,2-O-dioleylglycerol,
3-O-(2-Piperidinoethyl)carbamoyl-1,2-O-dioleylglycerol,
3-O-(2-Pyrrolidinoethyl)carbamoyl-1,2-O-dioleylglycerol,
3-O-(2-Diethylaminoethyl)thiocarbamoyl-1,2-O-dioleylglycerol,
3-O-(2-Dimethylaminoethyl)thiocarbamoyl-1,2-O-dioleylglycerol,
3-O-[2-(N,N-Di-(2-hydroxyethyl)amino)ethyl]thiocarbamoyl-1,2-O-dioleylglycerol,
3-O-(2-Pyrrolidinoethyl)thiocarbamoyl-1,2-O-dioleylglycerol,
3-O-(2-Dimethylaminoethyl)sulfamoyl-1,2-O-dioleylglycerol,
3-O-(2-Diethylaminoethyl)sulfamoyl-1,2-O-dioleylglycerol,
3-O-[2-N,N-Di-(2-hydroxyethyl)amino)ethyl]sulfamoyl-1,2-O-dioleylglycerol,
3-O-(2-Pyrrolidinoethyl)sulfamoyl-1,2-O-dioleylglycerol,
3-O-(N,N-Dimethylaminoacetyl)-1,2-O-dioleylglycerol,
3-O-(4-Dimethylaminobutanoyl)-1,2-O-dilaurylglycerol,
3-O-(4-Diethylaminobutanoyl)-1,2-O-dipalmitylglycerol,
3-O-(4-diemthylaminobutanoyl)-1,2-O-dioleylglycerol, 3-O-(4-Diethylaminobutanoyl)-1,2-O-dioleylglycerol,
3-O-(4-Dimethylaminobutanoyl)-1,2-O-dilinoleylglycerol,
3-O-(4-Dimethylaminobutanoyl)-1-O-oleyl-2-O-palmitylglycerol,
3-O-(4-Dimethylaminobutanoyl)-1-O-linoleyl-2-O-oleylglycerol,
3-O-(3-Dimethylaminopropionyl)-1,2-O-dioleylglycerol,
3-O-(5-Dimethylaminopentanoyl)-1,2-O-dioleylglycerol,
3-O-(4-Di-n-propylaminobutanoyl)-1,2-O-dioleylglycerol,
3-O-(4-Diisopropylaminobutanoyl)-1,2-O-dioleylglycerol,
3-O-[4-(N-Ethyl-N-methylamino)butanoyl]-1,2-O-dioleylglycerol,
3-O-[4-Ethylaminobutanoyl)-1,2-O-dioleylglycerol,
3-O-[4-(N-Methyl-N-(2-hydroxyethyl)amino)butanoyl]-1,2-O-dioleylglycerol,
3-O-[4-(N,N-Di-(2-hydroxyethyl)amino)butanoyl]-1,2-O-dioleylglycerol,
3-O-[4-(N-(2-Diethylamino)ethyl-N-methylamino)butanoyl]-1,2-O-dioleylglycerol,
3-O-[4-(4-Methylpiperazino)butanoyl]-1,2-O-dioleylglycerol,
3-O-(4-Morpholinobutanoyl)-1,2-O-dioleylglycerol,
3-O-(4-Pyrrolidinobutanoyl)-1,2-O-dioleylglycerol,
3-O-(4-Piperidinobutanoyl)-1,2-O-dioleylglycerol,
O-(2-Diethylaminoethyl)-O'-(2,3-dioleyloxypropyl) methylphosphonate,
O-(2-Dimethylaminoethyl)-O'-(2,3-dioleyloxypropyl) methylphosphonate,
O-[2-(N,N-di(2-hydroxyethyl)amino)ethyl]-O'-(2,3-dioleyloxypropyl) methylphosphonate,
O-(2-Pyrrolidinoethyl)-O'-(2,3-dioleyloxypropyl) methylphosphonate,
3-O-(2-Dimethylaminoethyl)carbamoyl-1,2-O-dilauroylglycerol,
3-O-(2-Dimethylaminoethyl)carbamoyl-1,2-O-dimyristoylglycerol,
3-O-(2-Dimethylaminoethyl)carbamoyl-1,2-O-dipalmitoylglycerol,
3-O-(2-Dimethylaminoethyl)carbamoyl-1,2-O-dioleoylglycerol,
3-O-(2-Dimethylaminoethyl)carbamoyl-1,2-O-dilinolenylglycerol,
3-O-(2-Dimethylaminoethyl)carbamoyl-1-O-oleoyl-2-O-palmitoylglycerol,
3-O-(2-Dimethylaminoethyl)carbamoyl-1-O-linolenyl-2-O-oleoylglycerol,
3-O-(3-Dimethylaminopropyl)carbamoyl-1,2-O-dioleoylglycerol,
3-O-(2-Diethylaminoethyl)carbamoyl-1,2-O-dioleoylglycerol,
3-O-(2-Di-n-propylaminoethyl)carbamoyl-1,2-O-dioleoylglycerol,
3-O-(2-Diisopropylaminoethyl)carbamoyl-1,2-O-dioleoylglycerol,
3-O-[2-(N-Ethyl-N-methylamino)ethyl]carbamoyl-1,2-O-dioleoylglycerol,
3-O-(2-Ethylaminoethyl)carbamoyl-1,2-O-dioleoylglycerol,
3-O-[2-(N-Methyl-N-(2-hydroxyethyl)amino)ethyl]carbamoyl-1,2-O-dioleoylglycerol,
3-O-[2-(N,N-Di-(2-hydroxyethyl)amino)ethyl]carbamoyl-1,2-O-dioleoylglycerol,
3-O-[2-(N-(2-Diethylamino)ethyl-N-methylamino)ethyl]carbamoyl-1,2-O-dioleoylglycerol,
3-O-(2-Piperidinoethyl)carbamoyl-1,2-O-dioleoylglycerol,
3-O-(2-Pyrrolidinoethyl)carbamoyl-1,2-O-dioleoylglycerol,
3-O-(2-Aminoethyl)carbamoyl-1,2-O-dioleoylglycerol
3-O-(2-Diethylaminoethyl)thiocarbamoyl-1,2-O-dioleoylglycerol,
3-O-(2-Dimethylaminoethyl)thiocarbamoyl-1,2-O-dioleoylglycerol,
3-O-[2-(N,N-Di-(2-hydroxyethyl)amino)ethyl]thiocarbamoyl-1,2-O-dioleoylglycerol,
3-O-(2-Pyrrolidinoethyl)thiocarbamoyl-1,2-O-dioleoylglycerol,
3-O-(2-Diethylaminoethyl)sulfamoyl-1,2-O-dioleoylglycerol,
3-O-(2-Dimethylaminoethyl)sulfamoyl-1,2-O-dioleoylglycerol,
3-O-[2-(N,N-Di-(2-hydroxyethyl)amino)ethyl]sulfamoyl-1,2-O-dioleoylglycerol,
3-O-(2-Pyrrolidinoethyl)sulfamoyl-1,2-O-dioleoylglycerol,
3-O-(4-Dimethylaminobutanoyl)-1,2-O-dilauroylglycerol,
3-O-(4-Dimethylaminobutanoyl)-1,2-O-dimyristoylglycerol,
3-O-(4-Dimethylaminobutanoyl)-1,2-O-dipalmitoylglycerol,
3-O-(4-Dimethylaminobutanoyl)-1,2-O-dioleoylglycerol,
3-O-(4-Dimethylaminobutanoyl)-1,2-O-dilinolenylglycerol,
3-O-(4-Dimethylaminobutanoyl)-1-O-oleoyl-2-O-palmitoylglycerol,
3-O-(4-Dimethylaminobutanoyl)-1-O-linolenyl-2-O-oleoylglycerol,
3-O-(3-Dimethylaminopropionyl)-1,2-O-dioleoylglycerol,
3-O-(5-Dimethylaminopentanoyl)-1,2-O-dioleoylglycerol,
3-O-(4-Diethylaminobutanoyl)-1,2-O-dioleoylglycerol,
3-O-(4-Di-n-propylaminobutanoyl)-1,2-O-dioleoylglycerol,
3-O-(4-Diisopropylaminobutanoyl)-1,2-O-dioleoylglycerol,
3-O-[4-(N-Ethyl-N-methylamino)butanoyl]-1,2-O-dioleoylglycerol,
3-O-(4-Ethylaminobutanoyl)-1,2-O-dioleoylglycerol,
3-O-[4-(N-Methyl-N-(2-hydroxyethyl)amino)butanoyl]-1,2-O-dioleoylglycerol,
3-O-[4-(N,N-Di-(2-hydroxyethyl)amino)butanoyl]-1,2-O-dioleoylglycerol,
3-O-[4-(N-(2-Diethylamino)ethyl-N-methylamino)butanoyl]-1,2-O-dioleoylglycerol
3-O-(4-Pyrrolidinobutanoyl)-1,2-O-dioleoylglycerol,
O-(2-Diethylaminoethyl)-O'-(2,3-dioleoyloxypropyl) methylphosphonate,
O-(2-Dimethylaminoethyl)-O'-(2,3-dioleoyloxypropyl) methylphosphonate,
O-[2-(N,N-Di-(2-hydroxyethyl)amino)ethyl]-O'-(2,3-dioleoyloxypropyl)methylphosphonate,
O-(2-Pyrrolidinoethyl)-O'-(2,3-dioleoyloxypropyl) methylphosphonate,
2-O-(2-Dimethylaminoethyl)carbamoyl-1,3-O-dilaurylglycerol,
2-O-(2-Dimethylaminoethyl)carbamoyl-1,3-O-dimyristylglycerol,
2-O-(2-Dimethylaminoethyl)carbamoyl-1,3-O-dipalmitylglycerol, 2-O-(2-Dimethylaminoethyl)carbamoyl-1,3-O-dioleylglycerol,
2-O-(2-Dimethylaminoethyl)carbamoyl-1,3-O-dilinoleylglycerol,
2-O-(2-Dimethylaminoethyl)carbamoyl-1-O-lauryl-3-O-myristylglycerol,
2-O-(2-Dimethylaminoethyl)carbamoyl-1-O-oleyl-3-O-palmitylglycerol,
2-O-(2-Dimethylaminoethyl)carbamoyl-1-O-linoleyl-3-O-oleylglycerol,
2-O-(3-Dimethylaminopropyl)carbamoyl-1,3-O-dioleylglycerol,
2-O-(4-Dimethylaminobutyl)carbamoyl-1,3-O-dioleylglycerol,
2-O-(2-Diethylaminoethyl)carbamoyl-1,3-O-dioleylglycerol,
2-O-(2-Di-n-propylaminoethyl)carbamoyl-1,3-O-dioleylglycerol,
2-O-(2-diisopropylaminoethyl)carbamoyl-1,3-O-dioleylglycerol,
2-O-(2-Di-n-butylaminoethyl)carbamoyl-1,3-O-dioleylglycerol,
2-O-(2-Diisobutylaminoethyl)carbamoyl-1,3-O-dioleylglycerol,
2-O-(2-Di-sec-butylaminoethyl)carbamoyl-1,3-O-dioleylglycerol,
2-O-[2-(N-Ethyl-N-methyl)aminoethyl]carbamoyl-1,3-O-dioleylglycerol,
2-O-(2-Methylaminoethyl)carbamoyl-1,3-O-dioleylglycerol,
2-O-(2-Ethylaminoethyl)carbamoyl-1,3-O-dioleylglycerol,
2-O-(2-n-Propylaminoethyl)carbamoyl-1,3-O-dioleylglycerol,
2-O-(2-Butylaminoethyl)carbamoyl-1,3-O-dioleylglycerol,
2-O-(2-Aminoethyl)carbamoyl-1,3-O-dioleylglycerol,
2-O-[2-(N-Methyl-N-(2-hydroxyethyl)amino)ethyl]carbamoyl-1,3-O-dioleylglycerol,
2-O-[2-(N-Ethyl-N-(2-hydroxyethyl)amino)ethyl]carbamoyl-1,3-O-dioleylglycerol,
2-O-(2-(N,N-Di-(2-hydroxyethyl)amino)ethyl]carbamoyl-1,3-O-dioleylglycerol,
2-O-[2-(N-(2-Diethylamino)ethyl-N-methylamino)ethyl]carbamoyl-1,3-O-dioleylglycerol,
2-O-[2-(4-Methylpiperazino)ethyl]carbamoyl-1,3-O-dioleylglycerol,
2-O-(2-Morpholinoethyl)carbamoyl-1,3-O-dioleylglycerol,
2-O-(2-Piperidinoethyl)carbamoyl-1,3-O-dioleylglycerol,
2-O-(2-Pyrrolidinoethyl)carbamoyl-1,3-O-dioleylglycerol,
2-O-(2-Dimethylaminoethyl)thiocarbamoyl-1,3-O-dioleylglycerol,
2-O-(2-Diethylaminoethyl)thiocarbamoyl-1,3-O-dioleylglycerol,
2-O-[2-(N,N-Di-(2-hydroxyethyl)amino)ethyl]thiocarbamoyl-1,3-O-dioleylglycerol,
2-O-(2-Pyrrolidinoethyl)thiocarbamoyl-1,3-O-dioleylglycerol,
2-O-(2-Dimethylaminoethyl)sulfamoyl-1,3-O-dioleylglycerol,
2-O-(2-Diethylaminoethyl)sulfamoyl-1,3-O-dioleylglycerol,
2-O-[2-(N,N-Di-(2-hydroxyethyl)amino)ethyl]sulfamoyl-1,3-O-dioleylglycerol,
2-O-(2-Pyrrolidinoethyl)sulfamoyl-1,3-O-dioleylglycerol,
2-O-(4-Dimethylaminobutanoyl)-1,3-O-dilaurylglycerol,
2-O-(4-Diethylaminobutanoyl)-1,3-O-dipalmitylglycerol,
2-O-(4-Dimethylaminobutanoyl)-1,3-O-dilinoleylglycerol,
2-O-(4-Dimethylaminobutanoyl)-1-O-oleyl-3-O-palmitylglycerol,
2-O-(4-Dimethylaminobutanoyl)-1-O-linoleyl-3-O-oleylglycerol,
2-O-(3-Dimethylaminopropionyl)-1,3-O-dioleylglycerol,
2-O-(5-Dimethylaminopentanoyl)-1,3-O-dioleylglycerol,
2-O-(4-Di-n-propylaminobutanoyl)-1,3-O-dioleylglycerol,
2-O-(4-Diisopropylaminobutanoyl)-1,3-O-dioleylglycerol,
2-O-[4-(N-Ethyl-N-methyl)aminobutanoyl]-1,3-O-dioleylglycerol,
2-O-(4-Ethylaminobutanoyl)-1,3-O-dioleylglycerol,
2-O-[4-(N-Methyl-N-(2-hydroxyethyl)amino)butanoyl]-1,3-O-dioleylglycerol,
2-O-[4-(N,N-Di-(2-hydroxyethyl)amino)butanoyl]-1,3-O-dioleylglycerol,
2-O-[4-(N-(2-Diethylamino)ethyl-N-methylamino)butanoyl]-1,3-O-dioleylglycerol,
2-O-[4-(4-Methylpiperazino)butanoyl]-1,3-O-dioleylglycerol,
2-O-(4-Morpholinobutanoyl)-1,3-O-dioleylglycerol,
2-O-(4-Pyrrolidinobutanoyl)-1,3-O-dioleylqlycerol,
2-O-(4-Piperidinobutanoyl)-1,3-O-dioleylglycerol,
O-(2-Diethylaminoethyl)-O'-(1-3-dioleyloxypropyl) methylphosphonate,
O-(2-Dimethylaminoethyl)-O'-(1,3-dioleyloxypropan-2-yl) methylphosphonate,
O-[2-(N,N-Di-(2-hydroxyethyl)amino)ethyl]-O'-(1,3-dioleyloxypropan-2-yl)methylphosphonate,
O-(2-Pyrrolidinoethyl)-O'-(1,3-dioleyloxypropan-2-yl) methylphosphonate,
2-O-(2-Dimethylaminoethyl)carbamoyl-1,3-O-dilauroylglycerol,
2-O-(2-Dimethylaminoethyl)carbamoyl-1,3-O-dimyristoylglycerol,
2-O-(2-Dimethylaminoethyl)carbamoyl-1,3-O-dipalmitoylglycerol,
2-O-(2-Diethylaminoethyl)carbamoyl-1,3-O-dipalmitoylglycerol,
2-O-(2-Dimethylaminoethyl)carbamoyl-1,3-O-dioleoylglycerol,
2-O-(2-Dimethylaminoethyl)carbamoyl-1,3-O-dilinolenylglycerol,
2-O-(2-Dimethylaminoethyl)carbamoyl-1-O-oleoyl-3-O-palmitoylglycerol,
2-O-(2-Dimethylaminoethyl)carbamoyl-1-O-linolenyl-3-O-oleoylglycerol,
2-O-(Dimethylaminomethyl)carbamoyl-1,3-O-dioleoylglycerol,
2-O-(3-Dimethylaminopropyl)carbamoyl-1,3-O-dioleoylglycerol,
2-O-(2-Diethylaminoethyl)carbamoyl-1,3-O-dioleoylglycerol,
2-O-(2-Di-n-propylaminoethyl)carbamoyl-1,3-O-dioleoylglycerol,
2-O-(2-Diisopropylaminoethyl)carbamoyl-1,3-O-dioleoylglycerol,
2-O-[2-(N-Ethyl-N-methylamino)ethyl]carbamoyl-1,3-O-dioleoylglycerol,
2-O-[2-(N-Methyl-N-n-butylamino)ethyl]carbamoyl-1,3-O-dioleoylglycerol, 2-O-(2-Ethylaminoethyl)carbamoyl-1,3-O-dioleoylglycerol,
2-O-[2-(N,N-Di-(2-hydroxyethyl)amino)ethyl]carbamoyl-1,3-O-dioleoylglycerol,
2-O-[2-(N-Methyl-N-(2-hydroxyethyl)amino)ethyl]carbamoyl-1,3-O-dioleoylglycerol,
2-O-[2-(N-Ethyl-N-(2-hydroxyethyl)amino)ethyl]carbamoyl-1,3-O-dioleoylglycerol,
2-O-[2-(N-2-Diethylamino)ethyl-N-methylamino)ethyl]carbamoyl-1,3-O-dioleoylglycerol,
2-O-[2-(N,N,N',N'-Tetramethylguanidino)ethyl]carbamoyl-1,3-O-dioleoylglycerol,
2-O-(2-Morpholinoethyl)carbamoyl-1,3-O-dioleoylglycerol,
2-O-(2-Piperidinoethyl)carbamoyl-1,3-O-dioleoylglycerol,
2-O-(2-Pyrrolidinoethyl)carbamoyl-1,3-O-dioleoylglycerol,
2-O-[2-(4-Ethylpiperazino)ethyl]carbamoyl-1,3-O-dioleoylglycerol,
2-O-[2-(4-(2-Hydroxyethyl)piperazino)ethyl]carbamoyl-1,3-O-dioleoylglycerol,
2-O-(2-Diethylaminoethyl)thiocarbamoyl-1,3-O-dioleoylglycerol,
2-O-(2-Dimethylaminoethyl)thiocarbamoyl-1,3-O-dioleoylglycerol,
2-O-[2-(N,N-Di-(2-hydroxyethyl)amino)ethyl]thiocarbamoyl-1,3-O-dioleoylglycerol,
2-O-(2-Pyrrolidinoethyl)thiocarbamoyl-1,3-O-dioleoylglycerol,
2-O-(2-Diethylaminoethyl)sulfamoyl-1,3-O-dioleoylglycerol,
2-O-(2-Dimethylaminoethyl)sulfamoyl-1,3-O-dioleoylglycerol,
2-O-[2-N,N-Di-(2-hydroxyethyl)aminoethyl]sulfamoyl-1,3-O-dioleoylglycerol,
2-O-(2-Pyrrolidinoethyl)sulfamoyl-1,3-O-dioleoylglycerol,
2-O-(3-Diethylaminopropionyl)-1,3-O-dioleoylglycerol,
2-O-(4-Dimethylaminobutanoyl)-1,3-O-dilauroylglycerol,
2-O-(4-Dimethylaminobutanoyl)-1,3-O-dimyristoylglycerol,
2-O-(4-Dimethylaminobutanoyl)-1,3-O-dipalmitoylglycerol,
2-O-(4-Dimethylaminobutanoyl)-1,3-O-dioleoylglycerol,
2-O-(4-Dimethylaminobutanoyl)-1,3-O-dilinolenylglycerol,
2-O-(4-Dimethylaminobutanoyl)-1-O-oleoyl-3-O-palmitoylglycerol,
2-O-(4-Dimethylaminobutanoyl)-1-O-linolenyl-3-O-oleoylglycerol,
2-O-(3-Dimethylaminopropionyl)-1,3-O-dioleoylglycerol,
2-O-(5-Dimethylaminopentanoyl)-1,3-O-dioleoylglycerol,
2-O-(4-Diethylaminobutanoyl)-1,3-O-dioleoylglycerol,
2-O-(4-Di-n-propylaminobutanoyl)-1,3-O-dioleoylglycerol,
2-O-(4-Diisopropylaminobutanoyl)-1,3-O-dioleoylglycerol,
2-O-[4-(N-Ethyl-N-methylamino)butanoyl]-1,3-O-dioleoylglycerol,
2-O-[4-(Ethyl)aminobutanoyl]-1,3-O-dioleoylglycerol,
2-O-[4-(N-Methyl-N-(2-hydroxyethyl)amino)butanoyl]-1,3-O-dioleoylglycerol,
2-O-[4-(N,N-Di-(2-hydroxyethyl)amino)butanoyl]-1,3-O-dioleoylglycerol,
2-O-[4-(N-(2-Diethylamino)ethyl-N-methylamino)butanoyl]-1,3-O-dioleoylglycerol,
2-O-(4-Pyrrolidinobutanoyl)-1,3-O-dioleoylglycerol,
O-(2-Dimethylaminoethyl)-O'-(1,3-dioleoyloxypropan-2-yl) methylphosphonate,
O-(2-Aminoethyl)-O'-(1,3-dioleoyloxypropan-2-yl) methylphosphonate,
O-(2-Diethylaminoethyl)-O'-(1,3-dioleoyloxypropan-2-yl) methylphosphonate,
2-Dimethylaminoethyl N-(2,3-dilauryloxypropyl) carbamate,
2-Dimethylaminoethyl N-(2,3-dimyristyloxypropyl) carbamate,
2-Dimethylaminoethyl N-(2,3-dioleyloxypropyl) carbamate,
2-Dimethylaminoethyl N-(2,3-dilinoleyloxypropyl) carbamate,
2-Dimethylaminoethyl N-(2-lauryloxy-3-linoleyloxypropyl) carbamate,
2-Dimethylaminoethyl N-(3-myristyloxy-2-oleyloxypropyl)carbamate,
3-Dimethylaminopropyl N-(2,3-dioleyloxypropyl) carbamate,
4-Dimethylaminobutyl N-(2,3-dioleyloxypropyl) carbamate,
2-Diethylaminoethyl N-(2,3-dioleyloxypropyl) carbamate,
2-Di-n-propylaminoethyl N-(2,3-dioleyloxypropyl) carbamate,
2-Di-n-butylaminoethyl N-(2,3-dioleyloxypropyl) carbamate,
2-Ethylmethylaminoethyl N-(2,3-dioleyloxypropyl) carbamate,
2-(N-Ethyl-N-methylamino)ethyl N-(2,3-dioleyloxypropyl) carbamate,
2-Ethylaminobutyl N-(2,3-dioleyloxypropyl)carbamate,
2-n-Propylaminoethyl N-(2,3-dioleyloxypropyl) carbamate,
2-[N-Methyl-N-(2-hydroxyethyl)amino]ethyl N-(2,3-dioleyloxypropyl)carbamate,
2-[N-Ethyl-N-(2-hydroxyethyl)amino]ethyl N-(2,3-dioleyloxypropyl) carbamate,
2-[N,N-Di-(2-hydroxyethyl)amino]ethyl N-(2,3-dioleyloxypropyl) carbamate,
2-[N-(2-Diethylamino)ethyl-N-methylamino]ethyl N-(2,3-dioleyloxypropyl)carbamate,
2-(4-Methylpiperadino)ethyl N-(2,3-dioleyloxypropyl) carbamate,
2-Morpholinoethyl N-(2,3-dioleyloxypropyl)carbamate,
2-Piperidinoethyl N-(2,3-dioleyloxypropyl)carbamate,
2-Pyrrolidinoethyl N-(2,3-dioleyloxypropyl)carbamate,
2-Dimethylaminoethyl N-(2,3-dioleyloxypropyl) thiocarbamate,
2-Diethylaminoethyl N-(2,3-dioleyloxypropyl) thiocarbamate,
2-[N,N-Di-(2-hydroxyethyl)amino]ethyl N-(2,3-dioleyloxypropyl) thiocarbamate,
2-Pyrrolidinoethyl N-(2,3-dioleyloxypropyl) thiocarbamate,
2-Dimethylaminoethyl N-(2,3-dioleyloxypropyl) sulfamate,
2-Diethylaminoethyl N-(2,3-dioleyloxypropyl)sulfamate,
2-[N,N-Di-(2-hydroxyethyl)amino]ethyl N-(2,3-dioleyloxypropyl) sulfamate,
2-Pyrrolidinoethyl N-(2,3-dioleyloxypropyl)sulfamate,
N-(2,3-Dioleyloxy)propyl-4-dimethylaminobutylamide,
N-(2,3-Dioleyloxy)propyl-4-diethylaminobutylamide, N-(2,3-Dioleyloxy)propyl-4-[N,N-di(2-hydroxyethyl)amino]butylamide,
N-(2,3-Dioleyloxy)propyl-4-pyrrolidinobutylamide,
2-Dimethylaminoethyl N-(2,3-dilauroyloxypropyl) carbamate,
2-Dimethylaminoethyl N-(2,3-dimyristoyloxypropyl) carbamate,
2-Dimethylaminoethyl N-(2,3-dipalmitoyloxypropyl) carbamate,
2-Dimethylaminoethyl N-(2,3-dioleoyloxypropyl) carbamate,
2-Dimethylaminoethyl N-(2,3-dilinolenyloxypropyl) carbamate,
2-Dimethylaminoethyl N-(2-oleoyloxy-3-palmitoyloxypropyl) carbamate,
2-Dimethylaminoethyl N-(2-linolenyloxy-3-oleoyloxypropyl) carbamate,
2-Diethylaminoethyl N-(2,3-dioleoyloxypropyl) carbamate,
3-Dimethylaminopropyl N-(2,3-dioleoyloxypropyl) carbamate,
2-Diisopropylaminoethyl N-(2,3-dioleoyloxypropyl) carbamate,
2-Di-n-propylaminoethyl N-(2,3-dioleoyloxypropyl) carbamate,
2-(N-Ethyl-N-methylamino)ethyl N-(2,3-dioleoyloxypropyl) carbamate,
2-Ethylaminoethyl N-(2,3-dioleoyloxypropyl)carbamate,
2-[N-methyl-N-(2-hydroxyethyl)amino]ethyl N-(2,3-dioleoyloxypropyl)carbamate,
2-[N,N-Di-(2-hydroxyethyl)amino]ethyl N-(2,3-dioleoyloxypropyl) carbamate,
2-[N-(2-Diethylamino)ethyl-N-methylamino]ethyl N-(2,3-dioleoyloxypropyl)carbamate,
2-Piperidinoethyl N-(2,3-dioleoyloxypropyl)carbamate,
2-Pyrrolidinoethyl N-(2,3-dioleoyloxypropyl)carbamate,
2-Aminoethyl N-(2,3-dioleoyloxypropyl)carbamate,
2-Dimethylaminoethyl N-(2,3-dioleoyloxypropyl) thiocarbamate,
2-Diethylaminoethyl N-(2,3-dioleoyloxypropyl) thiocarbamate,
2-[N,N-Di-(2-hydroxyethyl)aminoethyl] N-(2,3-dioleoyloxypropyl) thiocarbamate,
2-Pyrrolidinoethyl N-(2,3-dioleoyloxypropyl) thiocarbamate,
2-Dimethylaminoethyl N-(2,3-dioleoyloxypropyl) sulfamate,
2-Diethylaminoethyl N-(2,3-dioleoyloxypropyl) sulfamate,
2-[N,N-Di-(2-hydroxyethyl)aminoethyl]N-(2,3-dioleoyloxypropyl) sulfamate,
2-Pyrrolidinoethyl N-(2,3-dioleoyloxypropyl)sulfamate,
N-(2,3-Dioleoyloxy)propyl-4-dimethylaminobutylamide,
N-(2,3-Dioleoyloxy)propyl-4-diethylaminobutylamide,
N-(2,3-Dioleoyloxy)propyl-4-[N,N-di-(2-hydroxyethyl)amino]butylamide,
N-(2,3-Dioleoyloxy)propyl-4-pyrrolidinobutylamide,
2-Dimethylaminoethyl N-(1,3-dilauryloxypropan-2-yl) carbamate,
2-Dimethylaminoethyl N-(1,3-dimyristyloxypropan-2-yl) carbamate,
2-Dimethylaminoethyl N-(1,3-dioleyloxypropan-2-yl) carbamate,
2-Dimethylaminoethyl N-(1,3-dilinoleyloxypropan-2-yl) carbamate,
2-Dimethylaminoethyl N-(1-lauryloxy-3-linoleyloxypropan-2-yl) carbamate,
2-Dimethylaminoethyl N-(1-myristyloxy-3-oleyloxypropan-2-yl) carbamate,
2-Dimethylaminoethyl N-(1-oleyloxy-3-palmityloxypropan-2-yl) carbamate,
3-Dimethylaminopropyl N-(1,3-dioleyloxypropan-2-yl) carbamate,
4-Dimethylaminobutyl N-(1,3-dioleyloxypropan-2-yl) carbamate,
2-Diethylaminoethyl N-(1,3-dioleyloxypropan-2-yl) carbamate,
2-Di-n-propylaminoethyl N-(1,3-dioleyloxypropan-2-yl) carbamate,
2-Di-n-butylaminoethyl N-(1,3-dioleyloxypropan-2-yl) carbamate,
2-(N-Ethyl-N-methylamino)ethyl N-(1,3-dioleyloxypropan-2-yl) carbamate,
2-Methylaminoethyl N-(1,3-dioleyloxypropan-2-yl) carbamate,
2-Ethylaminobutyl N-(1,3-dioleyloxypropan-2-yl) carbamate,
2-n-Propylaminoethyl N-(1,3-dioleyloxypropan-2-yl) carbamate,
2-n-Butylamino N-(1,3-dioleyloxypropan-2-yl) carbamate,
2-[N-Methyl-N-(2-hydroxyethyl)amino]ethyl N-(1,3-dioleyloxypropan-2-yl)carbamate,
2-[N-Ethyl-N-(2-hydroxyethyl)amino]ethyl N-(1,3-dioleyloxypropan-2-yl)carbamate,
2-[N,N-Di-(2-hydroxyethyl)amino]ethyl N-(1,3-dioleyloxypropan-2-yl)carbamate,
2-[N-(2-Diethylamino)ethyl-N-methylamino]ethyl N-(1,3-dioleyloxypropan-2-yl)carbamate,
2-(4-Methylpiperadino)ethyl N-(1,3-dioleyloxypropan-2-yl) carbamate,
2-Piperidinoethyl N-(1,3-dioleyloxypropan-2-yl) carbamate,
2-Pyrrolidinoethyl N-(1,3-dioleyloxypropan-2-yl) carbamate,
2-Dimethylaminoethyl N-(1,3-dioleyloxypropan-2-yl) thiocarbamate,
2-Diethylaminoethyl N-(1,3-dioleyloxypropan-2-yl) thiocarbamate,
2-[N,N-Di-(2-hydroxyethyl)amino]ethyl N-(1,3-dioleyloxypropan-2-yl)thiocarbamate,
2-Pyrrolidinoethyl N-(1,3-dioleyloxypropan-2-yl) thiocarbamate,
2-Dimethylaminoethyl N-(1,3-dioleyloxypropan-2-yl) sulfamate,
2-Diethylaminoethyl N-(1,3-dioleyloxypropan-2-yl) sulfamate,
2-[N,N-Di-(2-hydroxyethyl)amino]ethyl N-(1,3-dioleyloxypropan-2-yl)sulfamate,
2-Pyrrolidinoethyl N-(1,3-Dioleyloxypropan-2-yl) sulfamate,
N-(4-Dimethylaminobutanoyl)-1,3-dioleyloxy-1-amino-propane,
N-(4-Diethylaminobutanoyl)-1,3-dioleyloxy-1-amino-propane,
N-[4-(N,N-Di-(2-hydroxyethyl)amino)butanoyl]-1,3-dioleyloxy-1-amino-propane,
N-4-Pyrrolidinobutanoyl-1,3-dioleyloxy-1-amino-propane,
2-Dimethylaminoethyl N-(1,3-dilauroyloxypropan-2-yl) carbamate,
2-Dimethylaminoethyl N-(1,3-dimyristoyloxypropan-2-yl)carbamate,
2-Dimethylaminoethyl N-(1,3-dipalmitoyloxypropan-2-yl)carbamate, 2-Dimethylaminoethyl N-(1,3-dioleoyloxypropan-2-yl) carbamate, 2-Dimethylaminoethyl N-(1,3-dilinolenyloxypropan-2-yl)carbamate, 2-Dimethylaminoethyl N-(1-oleoyloxy-3-palmitoyloxypropan-2-yl) carbamate, 2-Dimethylaminoethyl N-(1-linolenyloxy-3-oleoyloxypropan-2-yl) carbamate, 2-Diethylaminoethyl N-(1,3-dioleoyloxypropan-2-yl) carbamate, 3-Dimethylaminopropyl N-(1,3-dioleoyloxypropan-2-yl) carbamate, 2-Diisopropylaminoethyl N-(1,3-dioleoyloxypropan-2-yl)carbamate, 2-Di-n-propylaminoethyl N-(1,3-dioleoyloxypropan-2-yl)carbamate, 2-(N-Ethyl-N-methylamino)ethyl N-(1,3-dioleoyloxypropan-2-yl) carbamate, 2-Ethylaminoethyl N-(1,3-dioleoyloxypropan-2-yl) carbamate, 2-[N-Methyl-N-(2-hydroxyethyl)amino]ethyl N-(1,3-dioleoyloxypropan-2-yl)carbamate, 2-[N,N-Di-(2-hydroxyethyl)amino]ethyl N-(1,3-dioleoyloxypropan-2-yl)carbamate, 2-[N-(2-Diethylamino)ethyl-N-methylamino]ethyl N-(1,3-dioleoyloxypropan-2-yl)carbamate, 2-Piperidinoethyl N-(1,3-dioleoyloxypropan-2-yl) carbamate, 2-Pyrrolidinoethyl N-(1,3-dioleoyloxypropan-2-yl) carbamate 2-Aminoethyl N-(1,3-dioleoyloxypropan-2-yl)carbamate, 2-Dimethylaminoethyl N-(1,3-dioleoyloxypropan-2-yl) thiocarbamate, 2-Diethylaminoethyl N-(1,3-dioleoyloxypropan-2-yl) thiocarbamate, 2-[N,N-Di-(2-hydroxyethyl)amino]ethyl N-(1,3-dioleoyloxypropan-2-yl)thiocarbamate, 2-Pyrrolidinoethyl N-(1,3-dioleoyloxypropan-2-yl) thiocarbamate, 2-Dimethylaminoethyl N-(1,3-dioleoyloxypropan-2-yl) sulfamate, 2-Diethylaminoethyl N-(1,3-dioleoyloxypropan-2-yl) sulfamate, 2-[N,N-Di-(2-hydroxyethyl)amino]ethyl N-(1,3-dioleoyloxypropan-2-yl)sulfamate, 2-Pyrrolidinoethyl N-(1,3-dioleoyloxypropan-2-yl) sulfamate, N-(2,3-Dioleoyloxy)propyl-4-dimethylaminobutylamide, N-(2,3-Dioleoyloxy)propyl-4-diethylaminobutylamide, N-(2,3-Dioleoyloxy)propyl-4-[N,N-di-(2-hydroxyethyl) amino]butylamide, N-(2,3-Dioleoyloxy)propyl-4-pyrrolidinobutylamide.

Among compounds of the invention, 3-O-(4-dimethylaminobutanoyl)-1,2-O-dioleylglycerol, 3-O-(2-dimethylaminoethyl)carbamyl-1,2-O-dioleylglycerol, 3-O-(2-diethylaminoethyl)carbamoyl-1,2-O-dioleylglycerol, 2-O-(2-diethylaminoethyl)carbamoyl-1,3-O-dioleoylglycerol, etc. are preferred. Particularly preferred is 3-O-(2-diethylaminoethyl)carbamoyl-1,2-O-dioleylglycerol.

Another essential feature of the present invention resides in the device comprising a compound [I] of the invention and a phospholipid and having the function of a DDS.

As lipid-containing devices having the function of a DDS, liposomes and fat emulsions are known. The device having the DDS function according to the present invention (hereinafter referred to as the device of the invention) belongs to the category of such devices.

The device of the invention may take any of various forms such as lipid suspension, liposome, etc. only if it has the property to transport a physiologically active substance into the cell.

The phospholipid as a component of the device of the invention may for example be phosphatidylethanolamine or phosphatidylcholine.

The ratio of the compound of the invention to the phospholipid in the present device is appropriately 0.1:9.9–9.9–0.1 (compound of the invention: phospholipid (molar ratio)), preferably 1:9–9:1 (compound of the invention: phospholipid (molar ratio)), and for still better results, 1:3–3:1 (compound of the invention phospholipid (molar ratio)).

The device of the invention can be manufactured by, for example, by the following method.

The device of the invention can be simply prepared typically by admixing the compound of the invention with the phospholipid in the presence of water. It can also be prepared by a process which comprises dissolving the compound of the invention and phospholipid in chloroform, removing the chloroform thoroughly under a blast of nitrogen gas, stirring the mixture well with addition of water, and subjecting it to sonication for several minutes.

Still another essential feature of the present invention resides in a pharmaceutical composition comprising the device of the invention and a physiologically active substance.

As mentioned hereinbefore, even a substance showing high physiological activity extracellularly cannot be expected to fully exhibit that activity if its intracellular penetration capacity is low, barring a dosage increase. The current state of the art is that for that reason many of potentially useful drugs cannot be clinically exploited. This is not only a great loss to the industry but also unfortunate from the standpoint of safeguarding the nation's health.

However, when administered along with the device of the invention, even a physiologically active substance with a poor intracellular penetration potential is allowed to enter into the cell with remarkable facility to display its activity to a sufficient extent. This means a substantial resuscitation of useful drugs so far left undeveloped.

Therefore, the pharmaceutical composition according to the present invention (hereinafter referred to as the composition of the invention) is of great use both industrially and in terms of the nation's health.

The device of the invention can be applied to physiologically active substances which are efficient in intracellular penetration. Even when a physiologically active substance with good intracellular penetrability is administered together with the device of the invention, a further enhancement of intracellular penetration is realized and, hence, its dosage can be decreased so that the risk of side effects can be diminished.

The physiologically active substance that can be applied to the device of the invention includes water-soluble anionic compounds, antitumor agents, antiviral agents and antibiotics, among others. To be specific, nucleic acid compounds such as double-stranded RNAs and double-stranded or triple-stranded antisense nucleic acids, acidic saccharides such as heparin sulfate and dextran sulfate, cytokines, second messengers such as cyclic AMP, ATP and IP3, penicillins and cephalosporins, vitamins such as vitamin C and retinols other known acidic group-containing drugs, interferons ($\alpha$, $\beta$, $\gamma$)., interleukins (IL-1, IL-2), colony stimulating factor (CSF), tumor necrosis factor (TNF), levamisole, bestatin, retinoic acid, 5-fluorouracil (5-FU), cytosine arabinoside (Ara-C), adenine arabinoside (Ara-A), cisplatin (CDDP), cyclophosphamide and azidothymidine (AZT), among others.

The double-stranded RNA includes but is not limited to the following compounds.

(1) Homopolymer-homopolymer Complexes
1 Base-modified
  Polyinosinic acid-polycytidylic acid.
  Polyinosinic acid-poly(5-bromocytidylic acid).
  Polyinosinic acid-poly(2-thiocytidylic acid).
  Poly(7-deazainosinic acid)-polycytidylic acid.
  Poly(7-deazainosinic acid-poly(5-bromocytidylic acid).
2 Ribose-modified
  Poly(2'-azidoinosinic acid)-polycytidylic acid.
3 Phosphate-modified
  Polyinosinic acid-poly(cytidine-5'-thiophosphate).
(2) Homopolymer-copolymer complexes
  Polyinosinic acid-poly(cytidylic acid-uridylic acid).
  Polyinosinic acid-poly(cytidylic acid-4-thiouridylic acid).
(3) Synthetic Nucleic acid-polycation Complexes
  Polyinosinic acid-polycytidylic acid-poly-L-lysine.
(4) Others
  Polyinosinic acid-poly(1-vinylcytidylic acid).

The antisense nucleic acid includes but is not limited to natural nucleic acids and derivatives thereof, such as nucleic acids having a methyl phosphonate, phosphorothioate or phosphorodithioate group as an internal bond and derivatives thereof.

The ratio of the device of the invention to the physiologically active substance is preferably 1:0.1–1:10 (device of the invention: physiologically active substance) by weight.

The composition of the invention can be prepared by adding a physiologically active substance to the device of the invention and agitating the mixture by suitable means. The composition may also be prepared by adding the physiologically active substance in the course of preparation of the device of the invention.

The composition of the invention is preferably administered in unit dosage forms and can be applied to animals including man by the intravenous, intraarterial, oral, intratissue, local (e.g. transdermal) or rectal route. Particularly preferred are intravenous administration, intraarterial administration, and local administration. Of course, the composition is administered in dosage forms suitable for the respective routes, such as injections, peroral preparations, inhalants, eyedrops, ointments, suppositories and so on.

While the dosage of the composition of the invention as a medicine is preferably determined in consideration of the species of active ingredient, dosage form, patient factors such as age and body weight, route of administration, nature and severity of disease, etc., the usual dosage for adults is generally 0.1 mg–10 g/day/man, preferably 1 mg–500 mg/day/man in terms of the active ingredient. A lower dosage may be sufficient in some cases, while a higher dosage may be needed in others. The dosage may be administered in a few divided doses or at intervals of a few days.

BEST MODE OF PRACTICING THE INVENTION

The following examples are intended to illustrate the present invention in further detail.

Reference Example 1

Synthesis of 1,2-O-dioleylglycerol (1) In 50 ml of pyridine was dissolved 4.6 g (50 mmol) of glycerol followed by addition of 13.9 g (50 mmol) of trityl chloride and the mixture was stirred at ambient temperature overnight. The reaction mixture was then concentrated under reduced pressure and the residue was diluted with water and extracted with ether. The organic layer was washed with water, dried over magnesium sulfate, and concentrated. The residue was purified by column chromatography (silica gel/chloroform-methanol) to provide 9.5 g (59%) of 1-O-tritylglycerol.

(2) In 120 ml of xylene was dissolved 3.22 g (10 mmol) of 1-O-tritylglycerol, followed by addition of 3.36 g (30 mmol) of t-butoxypotassium under argon. After 5 minutes of stirring, 30 ml of a solution of 12.8 g (30 mmol) oleyl p-toluenesulfonate in xylene was added dropwise and the mixture was stirred under reduced pressure (20–30 mmHg) at ambient temperature for 30 minutes and, then, at 50 for 1 hour. The reaction mixture was then poured in ice-water and extracted with ether, and the extract was washed with water, dried, and concentrated. The residue was purified by column chromatography silica gel/n-hexane-ethyl acetate) to provide 6.10 g (73%) of 1,2-O-dioleyl-3-O-tritylglycerol.

(3) 1,2-O-Dioleyl-3-O-tritylglycerol (6.10 g, 7.3 mmol) was reacted with 5% trichloroacetic acid/methylene chloride (50 ml, w/v) at ambient temperature for 1 hour. The organic layer was then washed with saturated aqueous sodium hydrogen carbonate solution and water, dried, and concentrated. The residue was purified by column chromatography (silica gel/chloroform) to provide 3.75 g (87%) of the title compound.

$^1$H-NMR (200 MHz, CDCl$_3$) δ: 0.88 (6H, t, J=6 Hz, C$\underline{H}_3$×2), 1.14–1.44 (44H, m, C$\underline{H}_2$×22), 1.48–1.68 (4H, m, OCH$_2$C$\underline{H}_2$×2), 1.90–2.10 (8$\underline{H}$, m, CH=CHC$\underline{H}_2$×4), 3.38–3.78 (9H, m, OC$\underline{H}_2$×4 & OCH), 5.26–5.45 (4$\underline{H}$, m, C$\underline{H}$=C$\underline{H}$×2)

MS (FAB): 593 (M+H)$^+$

Reference Example 2

Synthesis of 2,3-dioleyloxypropylamine (1) To a mixture of 1.00 g (1.7 mmol) of 1,2-O-dioleylglycerol, 0.83 g (17 mmol) of lithium azide, 0.89 g (3.4 mmol) of triphenylphosphine, and 1.13 g (3.4 mmol) of carbon tetrabromide was added 10 ml of N,N-dimethylformamide in bolus and the mixture was stirred at ambient temperature for 3 hours. After completion of the reaction, the solvent was distilled off and the residue was diluted with water and extracted with ether. The ether layer was washed with water, dried, and concentrated, and the residue was purified by column chromatography (silica gel/n-hexane-ethyl acetate) to provide 1.03 g (100%) of 2,3-dioleyloxypropyl azide as oil.

IR(neat, cm$^{-1}$): 2920, 2850, 2100

(2) In 30 ml of tetrahydrofuran was suspended 75 mg (2 mmol) of lithium aluminum hydride. While this suspension was held under ice-cooling, 1.03 g (1.7 mmol) of 2,3-dioleyloxypropyl azide was added dropwise and the mixture was stirred for 30 minutes. Then, the mixture was further stirred at ambient temperature for 2 hours. At completion of the reaction, the reaction mixture was poured in ice-water and extracted with ether and the extract was washed with water, dried, and concentrated. The residue was subjected to column chromatography (silica gel/methylene chloride-methanol) to provide 0.98 g (98%) of the title compound as colorless oil.

$^1$H-NMR (200 MHz, CDCl$_3$) δ: 0.88 (6H, t, J=6 Hz, CH$_3$×2), 1.17–1.45 (44H, m, CH$_2$×22), 1.48–1.70 (4H, m, OCH$_2$ C$\underline{H}_2$×2), 1.90–2.14 (8H, m, CH=CHC$\underline{H}_2$×4), 2.64–2.91 (2H, m, NCH$_2$), 3.30–3.78 (9H, m, OCH$_2$×3 & OCH), 5.25–5.46 (4H, m, CH=CH×2)

MS (FAB): 592 (M+H)$^+$

Reference Example 3

Synthesis of 1,3-O-dioleylglycerol (1) In pyridine were dissolved 1.00 g (11 mmol) of glycerol and 2.96 g (43 mmol) of imidazole and azeotropic distillation was carried out. The residue obtained was dissolved in 15 ml of N,N-dimethylformamide. To this solution under ice-cooling was added 3.60 g (24 mmol) of tributyldimethylsilyl chloride, and the mixture was stirred at ambient temperature for 5 hours. After completion of the reaction, the solvent was distilled off and the residue was diluted with methylene chloride and washed with saturated aqueous sodium hydrogen carbonate solution. This was dried and concentrated to provide 3.45 g (99%) of 1,3-O-di-(t-butyldimethylsilyl)glycerol.

(2) In dioxane was dissolved 3.45 g (11 mmol) of 1,3-O-di-(t-butyldimethylsilyl)glycerol followed by addition of 3.03 g (12 mmol) of pyridinium p-toluenesulfonate. To this suspension was added 16.5 ml (22 mmol) of dihydrofuran gradually under ice-cooling and the mixture was stirred for 1 hour. After return to ambient temperature, the mixture was allowed to react overnight. After completion of the reaction, the solvent was distilled off and the residue was treated with methylene chloride and saturated aqueous sodium hydrogen carbonate solution. The methylene chloride layer was washed with water, dried, and concentrated to provide 4.25 g (100%) of 1,3-O-di-(t-butyldimethylsilyl)-2-O-tetrahydrofuranylglycerol.

(3) To a solution of 4.25 g (11 mmol) 1,3-O-di-(t-butyldimethylsilyl)-2-O-tetrahydrofuranylglycerol in 30 ml tetrahydrofuran was added 30 ml of tetra-n-butylammonium fluoride (1 mol/1 in THF) dropwise and the mixture was stirred at ambient temperature for 2 hours. The reaction mixture was then concentrated and the residue was subjected to column chromatography (silica gel/methylene chloride-methanol) to provide 1.70 g (96%) of 2-O-tetrahydrofuranylglycerol.

(4) In 30 ml of xylene was dissolved 854 mg (5.3 mmol) of 2-O-tetrahydrofuranylglycerol. To this was added 1.78 g (15.9 mmol) of t-butoxypotassium under argon gas and the mixture was stirred for 5 minutes. Then, 10 ml of a solution of 6.71 g (15.9 mmol) oleyl p-toluenesulfonate in xylene was added dropwise and the mixture was stirred under reduced pressure (20–30 mmHg) at ambient temperature for 30 minutes and further at 50° C. for 1 hour. This reaction mixture was poured in ice-water and extracted with ether, and the extract was washed with water, dried, and concentrated. The residue was purified by column chromatography (silica gel/chloroform) to provide 628 mg (18%) of 1,3-O-dioleyl-2-O-tetrahydrofuranylglycerol as yellow oil. (5) In 30 ml of tetrahydrofuran was dissolved 628 mg (0.95 mmol) of 1,3-O-dioleyl-2-O-tetrahydrofuranylglycerol followed by addition of 5 ml of diluted (10%) hydrochloric acid, and the mixture was stirred overnight. The reaction mixture was then diluted with water, neutralized with saturated aqueous sodium hydrogen carbonate solution, and extracted with ether. The extract was dried and concentrated and the residue was subjected to column chromatography (silica gel/n-hexane-ethyl acetate) to provide 321 mg (57%) of the title compound as colorless oil.

$^1$H-NMR (200 MHz, CDCl$_3$) δ: 0.88 (6H, t, J=6 Hz, CH$_3$×2), 1.14–1.26 (44H, m, CH$_2$×22), 1.49–1.68 (4H, m, OCH$_2$CH$_2$×2), 1.98–2.13 (8H, m, CH=CHCH$_2$×4), 3.37–3.56 (8H, m, OCH$_2$×4), 3.95 (1H, brs, OCH), 5.27–5.46 (4H, m, CH=CH×2)

MS (FAB): 593 (M+H)$^+$

Reference Example 4

Synthesis of 1,3-dioleyloxy-2-propylamine (1) In 5 ml of pyridine was dissolved 150 mg (0.25 mmol) of 1,3-O-dioleylglycerol followed by addition of 77 mg (0.40 mmol) of p-toluenesulfonyl chloride and the mixture was heated at 60° C. and stirred for 2 days. After completion of the reaction, the solvent was distilled off and the residue was diluted with water and extracted with ether. The extract was dried and concentrated to provide 150 mg (80%) of 1,3-O-dioleyl-2-O-(p-toluenesulfonyl) glycerol as yellow oil.

(2) A mixture of 150 mg (80%) of the above 1,3-O-dioleyl-2-O-(p-toluenesulfonyl)glycerol, 30 mg (0.6 mmol) of lithium azide, and 5 ml of N,N-dimethylformamide was stirred at 100 ° C. for 2 hours. After cooling, the solvent was distilled off and the residue was diluted with water and extracted with ether. The extract was washed with water, dried, and concentrated to provide 125 mg (99%) of 1,3-dioleyloxy-2-propyl azide as light-brown oil.

(3) In 3 ml of tetrahydrofuran was suspended 8 mg (0.2 mmol) of lithium aluminum hydride. While this suspension was maintained under ice-cooling, 125 mg (0.2 mmol) of 1,3-dioleyloxy-2-propyl azide was added dropwise and the mixture was stirred at 0° C. for 2 hours. The reaction mixture was then poured in ice-water and extracted with ether. The extract was washed with water, dried, and concentrated. The residue was subjected to column chromatography (silica gel/methylene chloride-methanol) to provide 104 mg (89%) of the title compound as colorless oil.

Reference Example 5

Synthesis of 1,2-O-dioleoylglycerol (1) In pyridine was dissolved 1 g (0.011 mol) of glycerin and azeotropic distillation was carried out. The residue was dissolved in 30 ml of pyridine, followed by addition of 4.05 g (0.012 mol) of dimethoxytrityl chloride under ice-cooling. The mixture was then stirred at ambient temperature overnight. After completion of the reaction, 5 ml of methanol was added and the mixture was stirred for 30 minutes, at the end of which time the solvent was distilled off. To the residue was added methylene chloride and the mixture was washed with saturated aqueous sodium hydrogen carbonate solution, dried, and concentrated. The residue was subjected to column chromatography (silica gel/methylene chloride-methanol, 0.1% pyridine) to provide 2.58 g (60.2%) of 1-O-dimethoxytritylglycerol.

(2) The 1-O-dimethoxytritylglycerol thus obtained, 290 mg (0.735 mmol), was subjected to azeotropic distillation with pyridine and the residue was dissolved in 5 ml of pyridine. Then, 669 mg (2.223 mmol) of oleoyl chloride was added with ice-cooling and the reaction was carried out at 50° C. for 6 hours. After completion of the reaction, the solvent was distilled off under reduced pressure and the residue was diluted with methylene chloride, washed with saturated aqueous sodium hydrogen carbonate solution, dried, and concentrated. The residue was subjected to column chromatography (silica gel/n-hexanemethylene chloride) to provide 519 mg (76.5%) of 1-O-dimethoxytrityl-2,3-O-dioleoylglycerol.

$^1$H-NMR (60 MHz, CDCl$_3$) δ: 0.88 (6H, m), 1.27 (40H, brs.), 1.50–1.70 (4H, m), 1.90–2.10 (8H, m), 3.10–3.30 (2H, m), 3.79 (6H, s), 4.20–4.40 (2H, m), 5.10–5.50 (5H, m), 6.70–7.40 (13H, m)

(3) The above 1-O-dimethoxytrityl-2,3-O-dioleoylglycerol, 218 mg (0.236 mmol), was dissolved in 10 ml of 5% formic acid-methylene chloride and the reaction was conducted for 10 minutes. The reaction mixture was then neutralized with saturated aqueous sodium hydrogen carbonate solution and the organic layer was further washed with saturated aqueous sodium hydrogen carbonate solution, dried, and concentrated. The residue was subjected to column chromatography (silica gel/n-hexane-methylene chloride-methanol) to provide 100 mg (68.0%) of the title compound.

$^1$H-NMR (200 MHz, CDCl$_3$) δ: 0.88 (6H, t, J=6 Hz), 1.28 (40H, brs.), 1.50–1.70 (4H, m), 1.90–2.10 (8H, m), 2.28–2.40 (4H, m), 3.72 (2H, d, J=6 Hz), 4.10–4.40 (2H, m), 5.00–5.12 (1H, m), 5.30–5.40 (4H, m)

MS (FAB): 621 (M+H)$^+$

Reference Example 6

Synthesis of 1,3-O-dioleoylglycerol (1) In 60 ml of pyridine was dissolved 2.75 g (0.013 mol) of 2-O-(t-butyldimethylsilyl)glycerol, followed by addition of 8.82 g (0.028 mol) of oleoyl chloride under ice-cooling. The reaction was conducted at 50° C. for 15 hours. After completion of the reaction, the solvent was distilled off and the residue was diluted with methylene chloride, washed with saturated aqueous sodium hydrogen carbonate solution, dried, and concentrated. The above procedure provided 1,3-O-dioleoyl-2-O-(t-butyldimethylsilyl)glycerol.

(2) To 1,3-O-dioleoyl-2-O-(t-butyldimethylsilyl)glycerol was added 266 ml of 0.1 M tetra-n-butylammonium fluoride-tetrahydrofuran and the reaction was carried out at ambient temperature for 30 minutes. After completion of the reaction, the solvent was distilled off under reduced pressure and the residue was diluted with methylene chloride, washed with water, dried, and concentrated. The residue was subjected to column chromatography (silica gel/ethyl acetate-n-hexane) to provide 3.97 g (48.0% based on 2-O-t-butyldimethylsilylglycerol) of the title compound.

$^1$H-NMR (200 MHz, CDCl$_3$) δ: 0.88 (6H, t, J=6 Hz), 1.28 (40H, brs.), 1.50–1.70 (4H, m), 1.90–2.10 (8H, m), 2.34 (4H, t, J=8 Hz), 4.10–4.22 (5H, m), 5.30–5.40 (4H, m)

MS (FAB): 621 (M+H)$^+$

Reference Example 7

Synthesis of 1,3-O-dioleoyl-2-O-(2-bromoethyl) carbamoylglycerol (1) In pyridine was dissolved 230 mg (0.37 mmol) of 1,3-O-dioleoylglycerol and the solution was subjected to azeotropic distillation. The residue was dissolved in 5 ml of pyridine and after 120 mg (0.740 mmol) of N,N'-carbonyldiimidazole was added, the mixture was stirred at ambient temperature for 3 hours. The solvent was then distilled off under reduced pressure and the residue was dissolved in methylene chloride, washed with 5% sodium dihydrogen phosphate-water, dried, and concentrated. The residue was dissolved in 10 ml of N,N-dimethylformamide and after 45 mg (0.737 mmol) of 2-aminoethanol was added, the mixture was stirred at ambient temperature overnight. After completion of the reaction, the solvent was distilled off and the residue was dissolved in methylene chloride, washed with 5% sodium dihydrogen phosphate, dried, and concentrated. The residue was subjected to column chromatography (silica gel/methylene chloride-methanol) to provide 204 mg (79.5%) of 1,3-O-dioleoyl-2-O-(2-hydroxyethyl) carbamoylglycerol.

$^1$H-NMR (200 MHz, CDCl$_3$) δ: 0.88 (6H, t, J=6 Hz), 1.28 (40H, brs.), 1.50–1.80 (4H, m), 1.90–2.10 (8H, m), 2.34 (4H, t, J=8 Hz), 3.28–3.40 (2H, m), 3.64–3.80 (2H, m), 4.20–4.40 (4H, m), 5.06–5.20 (2H, m), 5.30–5.50 (4H, m)

MS (FAB): 690 (M–OH)$^+$ (2) To a mixture of 160 mg (0.226 mmol) 1,3-O-dioleoyl-2-O-(2-hydroxyethyl)carbamoylglycerol, 150 mg (0.452 mmol) of carbon tetrachloride, and 120 mg (0.458 mmol) of triphenylphosphine was added 10 ml of N,N-dimethylformamide in bolus and the mixture was stirred at ambient temperature for 2 hours. After completion of the reaction, the solvent was distilled off and the residue was dissolved in methylene chloride, washed with water, dried, and concentrated. The residue was subjected to column chromatography (silica gel/ethyl acetate-n-hexane) to provide 91 mg (52.2%) of the title compound.

$^1$H-NMR (200 MHz, CDCl$_3$) δ: 0.86 (6H, t, J=6 Hz), 1.28 (4OH, brs.), 1.50–1.70 (4H, m), 1.90–2.10 (8H, m), 2.31 (4H, t, J=8 Hz), 3.40–3.52 (2H, m), 3.52–3.70 (2H, m), 4.20–4.44 (4H, m), 5.06–5.20 (2H, m), 5.25–5.40 (4H, m)

MS (FAB): 770 (M+H)$^+$

EXAMPLE 1

Synthesis of 3-O-(2-dimethylaminoethyl)carbamoyl-1,2-O-dioleylglycerol

To 25 ml of a solution of 2.00 g (3.4 mmol) of 1,2-O-dioleylglycerol in pyridine was added 0.66 g (4.1 mmol) of N,N'-carbonyldiimidazole and the mixture was stirred at ambient temperature for 5 hours. The solvent was then distilled off under reduced pressure and the residue was dissolved in methylene chloride, washed with 5% sodium dihydrogen phosphate-water, dried, and concentrated. The residue was dissolved in 20 ml of N,N-dimethylformamide, and after addition of 595 mg (6.8 mmol) of N,N-dimethylethylenediamine, the mixture was stirred overnight. After completion of the reaction, the solvent was distilled off and the residue was diluted with water and extracted with methylene chloride. The extract was washed with water, dried, and concentrated and the residue was subjected to column chromatography (silica gel/chloroform-methanol) to provide 2.18 g (91%) of the title compound of the invention.

$^1$H-NMR (200 MHz, CDCl$_3$) δ: 0.88 (6H, t, J=7 Hz, CH$_3$×2), 1.16–1.44 (44H, m, CH$_2$×22), 1.47–1.68 (4H, m, OCH$_2$CH$_2$×2), 1.84–2.12 (8H, m, CH=CHCH$_2$×4), 2.20 (6H, s, $\overline{\text{N(CH}_3\text{)}_2}$), 2.39 (2H, t, J=6 Hz, NCH$_2$), 3.18–3.31 (2H, m, CONHC H$_2$), 3.36–3.64 (7H, m, OCH$_2$×3 & OCH), 4.03–4.26 (2H, m, CH$_2$OCO), 5.22 (1H, brs., NHCO), 5.28–5.43 (4H, m, CH=CH×2)

MS (FAB): 707 (M+H)$^+$

EXAMPLE 2

Synthesis of 3-O- (2-methylaminoethyl )carbamoyl-1,2-O-dioleylglycerol

The title compound of the invention was obtained in the same manner as Example 1 except that N-methylethylenediamine was used in lieu of N,N-dimethylethylenediamine.

$^1$H-NMR (200 MHz, CDCl$_3$) δ: 0.88 (6H, t, J=6 Hz), 1.28 (44H, brs.), 1.50–1.60 (4H, m), 1.90–2.10 (8H, m), 2.43 (3H, s), 2.71 (2H, t, J=6 Hz), 3.28 (2H, q, J=6 Hz), 3.40–3.70 (7H, m), 4.05–4.26 (2H, m), 5.14 (1H, brs.), 5.30–5.44 (4H, m)

MS (FAB): 693 (M+H)$^+$

EXAMPLE 3

Synthesis of 3-O-(2-aminoethyl)carbamoyl-1,2-O-dioleylglycerol

The compound synthesized using N-tritylethylenediamine in lieu of N,N-dimethylethylenediamine in otherwise the same manner as Example 1 was treated with 5% trichloroacetic acid-methylene chloride and purified in the same manner to provide the title compound of the invention.

$^1$H-NMR (200 MHz, CDCl$_3$) δ: 0.88 (6H, t, J=6 Hz), 1.28 (44H, brs.), 1.50–1.60 (4H, m), 1.90–2.10 (8H, m), 3.10–3.20 (2H, m), 3.40–3.70 (9H, m), 4.04–4.26 (2H, m), 5.30–5.45 (4H, m), 6.20 (1H, brs.)

MS (FAB): 679 (M+H)$^+$

EXAMPLE 4

Synthesis of 3-O-(2-diethylaminoethyl)carbamoyl-1,2-O-dioleylglycerol

Using N,N-diethylethylenediamine in lieu of N,N-dimethylethylenediamine, the procedure of Example 1 was otherwise repeated to provide the title compound of the invention.

$^1$H-NMR (200 MHz, CDCl$_3$) δ: 0.87 (6H, t, J=6 Hz), 1.01 (6H, t, J=6 Hz), 1.27 (44H, brs.), 1.46–1.62 (4H, m), 1.90–2.10 (8H, m), 2.48–2.62(6H, m), 3.18–3.30 (2H, m), 3.38–3.66 (7H, m), 4.04–4.24 (2H, m), 5.24–5.44 (5H, m)

MS (FAB): 735 (M+H)$^+$

EXAMPLE 5

Synthesis of 3-O-(4-dimethylaminobutyl)carbamoyl-1,2-O-dioleylglycerol

Using 4-dimethylaminobutylamine in lieu of N,N-dimethylethylenediamine, the procedure of Example 1 was otherwise repeated to provide the title compound of the invention.

$^1$H-NMR (200 MHz, CDCl$_3$) δ: 0.88 (6H, t, J=6 Hz), 1.28 (44H, brs.), 1.46–1.70 (8H, m), 1.90–2.10 (8H, m), 2.39 (6H, s), 2.44–2.56 (2H, m), 3.10–3.24 (2H, m), 3.36–3.70 (7H, m), 4.00–4.24 (2H, m), 5.18–5.42 (5H, m)

MS (FAB): 736 (M+H)$^+$

EXAMPLE 6

Synthesis of 3-O-(2-dimethylaminoethyl)thiocarbamoyl-1,2-O-dioleylglycerol

Using N,N'-thiocarbonyldiimidazole in lieu of N,N'-carbonyldiimidazole, the procedure of Example 1 was otherwise repeated to provide the title compound of the invention.

$^1$H-NMR (200 MHz, CDCl$_3$) δ: 0.88 (6H, t, J=6 Hz), 1.28 (44H, brs.), 1.50–1.60 (4H, m), 1.90–2.10 (8H, m), 2.21 (6H, d, J=4 Hz), 2.36–2.54 (2H, m), 3.30–3.80 (9H, m), 4.40–4.70 (2H, m), 5.26–5.45 (4H, m)

MS (FAB): 723 (M+H)$^+$

EXAMPLE 7

Synthesis of 3-O-(4-dimethylaminobutanoyl)-1,2-O-dioleylglycerol

In 6 ml of methylene chloride-N,N-dimethylformamide (1:2) was dissolved 120 mg (0.20 mmol) of 1,2-O-dioleylglycerol, followed by addition of 168 mg (1 mmol) of 4-dimethylaminobutyric acid hydrochloride. Then, 206 mg (1 mmol) of N,N'-dicyclohexylcarbodiimide (DCC) and 25 mg (0.2 mmol) of 4-dimethylaminopyridine were further added and the reaction was conducted at ambient temperature overnight. The precipitated byproduct urea was filtered off using a glass filter and the filtrate was concentrated to dryness under reduced pressure and treated with methylene chloride-saturated aqueous sodium hydrogen carbonate solution. After phase separation, the methylene chloride layer was dried over sodium sulfate and the solvent was distilled off under reduced pressure. The residue was subjected to column chromatography (silica gel/methylene chloride-methanol) to provide 123 mg (87%) of the title compound of the invention.

$^1$H-NMR (200 MHz, CDCl$_3$) δ: 0.88 (6H, t, J=6 Hz), 1.20–1.40 (44H, m), 1.45–1.60 (4H, m), 1.70–1.90 (2H, m), 1.90–2.10 (8H, m), 2.22 (6H, s), 2.30 (2H, t, J=8 Hz), 2.36 (2H, t, J=8 Hz), 3.38–3.85 (7H, m), 4.04–4.30 (2H, m), 5.30–5.45 (4H, m)

MS (FAB): 706 (M+H)$^+$

EXAMPLE 8

Synthesis of 3-O-(N,N-dimethylaminoacetyl)-1,2-O-dioleylglycerol

In a solvent mixture of 22 ml N,N-dimethylformamide and 11 ml methylene chloride was suspended 572 mg (5.547 mmol) of N,N-dimethylglycine followed by addition of 1736 mg (8.414 mmol) of N,N'-dicyclohexylcarbodiimide and the mixture was stirred at ambient temperature overnight. The solvent was then distilled off under reduced pressure and the residue was dissolved in 12 ml of pyridine containing 327 mg (0.551 mmol) of dissolved 1,2-O-dioleylglycerol. Then, 80 mg (0.388 mmol) of N,N'-dicyclohexylcarbodiimide (DCC) was added and the reaction was conducted at 50° C. overnight. After completion of the reaction, the solvent was distilled off and the residue was dissolved in methylene chloride, washed with saturated aqueous sodium hydrogen carbonate solution, dried, and concentrated. The residue was subjected to column chromatography (silica gel/ethyl acetate-n-hexane) to provide 251 mg (67.2%) of the title compound of the invention.

$^1$H-NMR (200 MHz, CDCl$_3$) δ: 0.88 (6H, t, J=6 Hz), 1.28 (44H, brs.), 1.50–1.70 (4H, m), 1.90–2.10 (8H, m), 2.36 (6H, s), 3.23 (2H, s), 3.40–3.70 (7H, m), 4.00–4.20 (2H, m), 5.20–5.40 (4H, m)

MS (FAB): 678 (M+H)$^+$

EXAMPLE 9

Synthesis of 3-O-(4-diethylaminobutanoyl)-1,2-O-dioleylglycerol (1) In 5 ml of anhydrous pyridine was dissolved 300 mg (0.51 mmol) of 1,2-O-dioleylglycerol, followed by addition of 188 mg (1.01 mmol) of 4-bromobutyl chloride under ice-cooling. After the temperature was allowed to return to ambient temperature, the reaction was conducted at 50° C. for 1 hour. The solvent was then distilled off and the residue was treated with methylene chloride-saturated aqueous sodium hydrogen carbonate solution. After phase separation and drying over sodium sulfate, the solvent was distilled off under reduced pressure. The residue thus obtained was subjected to column chromatography (silica gel/methylene chloride-methanol) to provide 159 mg (42%) of the bromo compound.

$^1$H-NMR (200 MHz, CDCl$_3$) δ: 0.88 (6H, t, J=6 Hz), 1.27 (44H, brs.), 1.50–1.70 (4H, m), 1.90–2.20 (10H, m), 2.53 (2H, t, J=8 Hz), 3.40–3.70 (9H, m), 4.05–4.30 (2H, m), 5.25–5.45 (4H, m)

(2) In 6 ml of N,N-dimethylformamide-isopropyl alcohol-chloroform (1:1:1) was dissolved 130 mg (0.18 mmol) of the above bromo compound followed by addition of 1 ml of diethylamine and 70 mg (0.54 mmol) of N,N-diisopropylethylamine. The mixture was reacted at 60° C. for 20 hours and at 80° C. for a further 6 hours. The solvent was then distilled off under reduced pressure and the residue was treated with methylene chloride-water. The methylene chloride layer was dried over sodium sulfate and concentrated under reduced pressure. The residue was subjected to column chromatography (silica gel/methylene chloride-methanol) to provide 63 mg (50%) of the title compound of the invention.

$^1$H-NMR (200 MHz, CDCl$_3$) δ: 0.88 (6H, t, J=6 Hz), 1.04 (6H, t, J=6 Hz), 1.27 (44H, brs.), 1.50–1.70 (4H, m), 1.80 (2H, m), 1.90–2.10 (8H, m), 2.37 (2H, t, J=6 Hz), 2.44–2.70 (6H, m), 3.40–3.70 (7H, m), 4.05–4.30 (2H, m), 5.30–5.45 (4H, m)

MS (FAB): 734 (M+H)$^+$

EXAMPLE 10

Synthesis of N-(2,3-dioleyloxy)propyl-4-dimethylaminobutylamide

In 3 ml of anhydrous N,N-dimethylformamide was dissolved 100 mg (0.17 mmol) of 2,3-dioleyloxypropylamine. To this solution were added 71 mg (0.42 mmol) of 4-dimethylaminobutyric acid hydrochloride, 105 mg (0.51 mmol) of N,N'-dicyclohexylcarbodiimide (DCC), and 4.1 mg (0.034 mmol) of 4-dimethylaminopyridine and the reaction was conducted at ambient temperature overnight. The reaction mixture was then treated as in Example 6 to provide 115 mg (96%) of the title compound of the invention.

$^1$H-NMR (200 MHz, CDCl$_3$) δ: 0.88 (6H, t, J=6 Hz), 1.20–1.40 (44H, m), 1.50–1.60 (4H, m), 1.70–1.90 (2H, m), 1.90–2.10 (8H, m), 2.23 (6H, s), 2.24 (2H, t, J=8 Hz), 2.34 (2H, t, J=8 Hz), 3.20–3.60 (9H, m), 5.30–5.42 (4H, m)

MS (FAB): 705 (M+H)$^+$

EXAMPLE 11

Synthesis of 3-O-(2-dimethylaminoethyl)sulfamoyl-1,2-O-dioleylglycerol

In 4 ml of methylene chloride-pyridine (2:1) was dissolved 150 mg (0.25 mmol) of 1,2-O-dioleylglycerol. Then, 1 ml of a solution of 150 mg (0.75 mmol) (2-dimethylaminoethyl)sulfamoyl chloride in methylene chloride was added and the reaction was carried out at ambient temperature for 2 hours. After completion of the reaction, the solvent was distilled off under reduced pressure and the residue was treated with methylene chloride-saturated aqueous sodium hydrogen carbonate solution. The methylene chloride layer was dried over sodium sulfate and concentrated under reduced pressure. The residue was subjected to column chromatography (silica gel/methylene chloride-methanol) to provide 34 mg (18%) of the title compound of the invention.

$^1$H-NMR (200 MHz, CDCl$_3$) δ: 0.88 (6H, t, J=6 Hz), 1.20–1.40 (44H, m), 1.45–1.65 (4H, m), 1.90–2.10 (8H, m), 2.24 (6H, s), 2.48 (2H, t, J=6 Hz), 3.18 (2H, t, J=6 Hz), 3.40–3.60 (6H, m), 3.60–3.75 (1H, m), 4.08–4.30 (2H, m), 5.30–5.40 (4H, m)

MS (FAB): 743 (M+H)$^+$

EXAMPLE 12

Synthesis of 2-dimethylaminoethyl N-(2,3-dioleyloxypropyl)carbamate

In 2 ml of pyridine was dissolved 45 mg (0.5 mmol) of 2-dimethylaminoethanol followed by addition of 97 mg (0.6 mmol) of N,N'-carbonyldiimidazole and the mixture was stirred for 4 hours. To this solution was added 355 mg (0.6 mmol) of 2,3-dioleyloxypropylamine dropwise and the mixture was stirred for 24 hours. After completion of the reaction, the solvent was distilled off and the residue was dissolved in methylene chloride, washed with saturated aqueous sodium hydrogen carbonate, dried, and concentrated. The residue was purified by column chromatography (silica gel/methylene chloride-methanol) to provide 383 mg (100%) of the title compound of the invention.

$^1$ H-NMR (200 MHz, CDCl$_3$) δ: 0.87 (6H, t, J=6 Hz, CH$_3$×2), 1.12–1.44 (44H, m, CH$_2$×22), 1.46–1.64 (4H, m, OCH$_2$CH$_2$×2), 1.88–2.12 (8H, m, CH=CHCH$_2$×4), 2.37 (6H, s, $\overline{N(CH_3)_2}$), 2.54 (2H, t, J=6 Hz, NC $\overline{H_2}$), 3.32–3.64 (9H, m, OCH$_2$×3, OCH and NHCH$_2$), 4.16 ($\overline{2H}$, t, J=6 Hz, COOCH$_2$), 5.17 (1H, brs., NH$\overline{CO}$), 5.26–5.46 (4H, m, CH=CH×2)

MS (FAB): 707 (M+H)$^+$

EXAMPLE 13

Synthesis of 2-O-(2-dimethylaminoethyl)carbamoyl-1,3-O-dioleylglycerol

To 2 ml of a solution of 150 mg (0.253 mmol) 1,3-O-dioleylglycerol in pyridine was added 82 mg (0.51 mmol) of N,N'-carbonyldiimidazole and the mixture was stirred at ambient temperature for 5 hours. The solvent was then distilled off under reduced pressure and the residue was dissolved in methylene chloride, washed with 5% sodium dihydrogen phosphate-water, dried, and concentrated. The residue was dissolved in 1.6 ml of N,N-dimethylform amide and stirred together with 45 mg (0.51 mmol) of N,N-dimethylethylenediamine overnight. After completion of the reaction, the solvent was distilled off and the residue was diluted with water and extracted with methylene chloride. The extract was washed with water, dried, and concentrated. The residue was subjected to column chromatography (silica gel/chloroform-methanol) to provide 179 mg (100%) of the title compound of the invention.

$^1$H-NMR (200 MHz, CDCl$_3$) δ: 0.88 (6H, t, J=6 Hz), 1.28 (44H, brs.), 1.50–1.65 (4H, m), 1.90–2.10 (8H, m), 2.20 (6H, s), 2.39 (2H, t, J=6 Hz), 3.20–3.30 (2H, m), 3.34–3.55 (4H, m), 3.55–3.70 (4H, d, J=4 Hz), 4.99 (1H, t, J=4 Hz), 5.25–5.46 (5H, m)

MS (FAB): 707 (M+H)$^+$

EXAMPLE 14

Synthesis of 2-dimethylaminoethyl N-(1,3-dioleyloxypropan-2-yl)carbamate

Using 1,3-dioleyloxy-2-propylamine, the procedure of Example 12 was otherwise repeated to provide the title compound of the invention.

$^1$H-NMR (200 MHz, CDCl$_3$) δ: 0.88 (6H, t, J=6 Hz), 1.28 (44H, brs.), 1.50–1.60 (4H, m), 1.90–2.10 (8H, m), 2.28 (6H, s), 2.54 (2H, t, J=6 Hz), 3.40–3.55 (8H, m), 3.80–3.90 (1H, m), 4.15 (2H, t, J=6 Hz), 5.10–5.20 (1H, m), 5.20–5.45 (4H, m)

MS (FAB): 707 (M+H)$^+$

EXAMPLE 15

Synthesis of 3-O-(2-dimethylaminoethyl)carbamoyl-1,2-O-dioleoylglycerol

Using 1,2-O-dioleoylglycerol, the procedure of Example 1 was otherwise repeated to provide the title compound of the invention.

$^1$H-NMR (200 MHz, CDCl$_3$) δ: 0.88 (6H, t, J=6 Hz), 1.28 (40H, brs.), 1.50–1.70 (4H, m), 1.90–2.10 (8H, m), 2.22 (6H, s), 2.24–2.40 (4H, m), 2.41 (2H, t, J=6 Hz), 3.20–3.30 (2H, m), 4.10–4.15 (4H, m), 5.20–5.30 (2H, m), 5.30–5.45 (4H, m)

MS (FAB): 735 (M+H)$^+$

EXAMPLE 16

Synthesis of 2-O-(2-dimethylaminoethyl)carbamoyl-1,3-O-dioleoylglycerol

Using 1,3-O-dioleoylglycerol, the procedure of Example 13 was otherwise repeated to provide the title compound of the invention.

$^1$H-NMR (200 MHz, CDCl$_3$) δ: 0.88 (6H, t, J=6 Hz), 1.26 (40H, brs.), 1.50–1.70 (4H, m), 1.90–2.10 (8H, m), 2.22 (6H, s), 2.32 (4H, t, J=8 Hz), 2.42 (2H, t, J=6 Hz), 3.20–3.30 (2H, m), 4.12–4.25 (4H, m), 5.15 (1H, t, J=6 Hz), 5.20–5.45 (5H, m)

MS (FAB): 735 (M+H)$^+$

EXAMPLE 17

Synthesis of 2-dimethylaminoethyl N-(2,3-dioleoyloxypropyl)carbamate

In 30 ml of anhydrous pyridine was dissolved 500 mg (5.61 mmol) of 2-dimethylaminoethanol followed by addition of 1.91 g (11.8 mmol) of N,N'-carbonyldiimidazole and the reaction was conducted at ambient temperature for 5 hours. To this reaction mixture was added 197 mg (2.16 mmol) of 3-amino-1,2-propanediol and the reaction was carried out at ambient temperature overnight. The pyridine was then distilled off under reduced pressure and the resulting crude carbamate was redissolved in anhydrous pyridine. Then, under ice-cooling, 5.22 g (17.4 mmol) of oleoyl chloride was added and the reaction was conducted at 50° C. for 14 hours. The pyridine was then distilled off under reduced pressure and the residue was dissolved in methylene chloride and washed with saturated aqueous sodium hydrogen carbonate solution. The methylene chloride layer was dried over sodium sulfate and concentrated. The residue was subjected to column chromatography (silica gel/methylene chloride-methanol) to provide 250 mg (16%) of the title compound of the invention.

$^1$H-NMR (200 MHz, CDCl$_3$) δ: 0.88 (6H, t, J=6 Hz), 1.25 (40H, brs.), 1.50–1.70 (4H, m), 1.90–2.10 (8H, m), 2.28 (6H, s), 2.30 (4H, t, J=8 Hz), 2.57 (2H, t, J=6 Hz), 3.30–3.50 (2H, m), 4.06–4.30 (4H, m), 5.04–5.15 (2H, m), 5.25–5.40 (4H, m)

MS (FAB): 735 (M+H)$^+$

EXAMPLE 18

Synthesis of 2-dimethylaminoethyl N-(1,3-dioleoyloxypropan-2-yl)carbamate

Using 2-amino-1,3-propanediol in lieu of 3-amino-1,2-propanediol, the procedure of Example 17 was otherwise repeated to provide 372 mg (2.2 mmol) of the title compound of the invention.

$^1$H-NMR (200 MHz, CDCl$_3$) δ: 0.87 (6H, t, J=7 Hz), 1.20–1.40 (40H, m), 1.50–1.70 (4H, m), 1.90–2.10 (8H, m), 2.30 (6H, s), 2.32 (4H, t, J=8 Hz), 2.59 (2H, t, J=6 Hz), 4.00–4.25 (7H, m), 5.10–5.20 (1H, m), 5.30–5.45 (4H, m)

MS (FAB): 735 (M+H)$^+$

EXAMPLE 19

Synthesis of 2-O-(2-piperidinoethyl)carbamoyl-1,3-O-dioleoylglycerol

Using 1,3-O-dioleoylglycerol and 1-(2-aminoethyl) piperidine, the procedure of Example 13 was otherwise repeated to provide the title compound of the invention $^1$H-NMR (200 MHz, CDCl$_3$) δ: 0.88 (6H, t, J=6 Hz), 1.28 (40H, brs.), 1.44–1.54 (2H, m), 1.54–1.76 (8H, m), 1.90–2.10 (8H, m), 2.32 (4H, t, J=8 Hz), 2.39–2.56 (6H, m), 3.20–3.40 (2H, m), 4.12–4.40 (4H, m), 5.08–5.24 (1H, m), 5.24–5.52 (5H, m)

MS (FAB): 773 (M+H)$^+$

EXAMPLE 20

Synthesis of 2-O-(2-diethylaminoethyl)carbamoyl-1,3-O-dioleoylglycerol

Using 1,3-O-dioleoylglycerol and N,N-diethylethylenediamine, the procedure of Example 13 was otherwise repeated to provide the title compound of the invention.

$^1$H-NMR (200 MHz, CDCl$_3$) δ: 0.88 (6H, t, J=6 Hz), 1.02 (6H, t, 6 Hz), 1.28 (40H, brs.), 1.50–1.70 (4H, m), 1.90–2.10 (8H, m), 2.32 (4H, t, J=8 Hz), 2.44–2.66 (6H, m), 3.16–3.32 (2H, m), 4.22–4.38 (4H, m), 5.08–5.22 (1H, m), 5.26–5.52 (5H, m)

MS (FAB): 763 (M+H)$^+$

EXAMPLE 21

Synthesis of 2-O-(2-diisopropylaminoethyl) carbamoyl-1,3-O-dioleoylglycerol

Using 1,3-O-dioleoylglycerol and N,N-diisopropylethylenediamine, the procedure of Example 13 was otherwise repeated to provide the title compound of the invention.

$^1$H-NMR (200 MHz, CDCl$_3$) δ: 0.88 (6H, t, J=6 Hz), 1.00 (12H, t, 6 Hz), 1.27 (40H, brs.), 1.50–1.70 (4H, m), 1.90–2.10 (8H, m), 2.30 (4H, t, J=8 Hz), 2.48–2.64 (2H, m), 2.88–3.20 (4H, m), 4.10–4.32 (4H, m), 5.06–5.28 (2H, m), 5.30–5.42 (4H, m)

MS (FAB): 791 (M+H)$^+$

EXAMPLE 22

Synthesis of 2-O-(2-pyrrolidinoethyl)carbamoyl-1,3-O-dioleoylglycerol

Using 1,3-O-dioleoylglycerol and 1-(2-aminoethyl) pyrrolidine, the procedure of Example 13 was otherwise repeated to provide the title compound of the invention.

$^1$H-NMR (200 MHz, CDCl$_3$) δ: 0.88 (6H, t, J=6 Hz), 1.27 (40H, brs.), 1.50–1.70 (4H, m), 1.74–1.88 (4H, m), 1.90–2.10 (8H, m), 2.30 (4H, t, J=8 Hz), 2.44–2.70 (6H, m), 3.20–3.40 (2H, m), 4.20–4.42 (4H, m), 5.08–5.22 (1H, m), 5.24–5.46 (5H, m)

MS (FAB): 761 (M+H)$^+$

EXAMPLE 23

Synthesis of 2-O-(2-morpholinoethyl)carbamoyl-1,3-O-dioleoylglycerol

Using 1,3-O-dioleoylglycerol and 4-(2-aminoethyl)morpholine, the procedure of Example 13 was otherwise repeated to provide the title compound of the invention.

$^1$H-NMR (200 MHz, CDCl$_3$) δ: 0.88 (6H, t, J=6 Hz), 1.27 (40H, brs.), 1.50–1.70 (4H, m), 1.90–2.10 (8H, m), 2.31 (4H, t, J=8 Hz), 2.40–2.54 (6H, m), 3.20–3.40 (2H, m), 3.70 (4H, t, J=6 Hz), 4.12–4.38 (4H, m), 5.08–5.20 (2H, m), 5.20–5.46 (4H, m)

MS (FAB): 777 (M+H)$^+$

EXAMPLE 24

Synthesis of 2-O-(3-diethylaminopropyl)carbamoyl-1,3-O-dioleoylglycerol

Using 1,3-O-dioleoylglycerol and 3-diethylaminopropylamine, the procedure of Example 13 was otherwise repeated to provide the title compound of the invention.

$^1$H-NMR (200 MHz, CDCl$_3$) δ: 0.88 (6H, t, J=6 Hz), 1.03 (6H, t, 6 Hz), 1.28 (40H, brs.), 1.50–1.70 (4H, m), 1.90–2.10 (8H, m), 2.30 (4H, t, J=8 Hz), 2.46–2.58 (6H, m), 3.20–3.32 (2H, m), 4.10–4.34 (4H, m), 5.10–5.20 (1H, m), 5.30–5.42 (4H, m), 6.18–6.30 (1H, brs.)

MS (FAB): 777 (M+H)$^+$

EXAMPLE 25

Synthesis of 2-O-[2-(N-methyl-N-(2-hydroxyethyl)amino)ethyl]carbamoyl-1,3-O-dioleoylglycerol In 10 ml of chloroform was dissolved 173 mg (0.224 mmol) of 1,3-O-dioleoyl-2-O-(2-bromoethyl)carbamoylglycerol followed by addition of 543 mg (7.228 mmol) of 2-(methylamino)ethanol and 27 mg (0.209 mmol of diisopropylethylamine and the mixture was refluxed at 80° C. overnight. The reaction mixture was then washed with 5% sodium dihydrogen phosphate-H$_2$O, dried, and concentrated. The residue was subjected to column chromatography (silica gel/methylene chloride-methanol) to provide 128 mg (74.3%) of the title compound of the invention.

$^1$H-NMR (200 MHz, CDCl$_3$) δ: 0.86 (6H, t, J=6 Hz), 1.27 (40H, brs.), 1.50–1.70 (4H, m), 1.90–2.10 (8H, m), 2.26–2.38 (7H, m), 2.50–2.70 (4H, m), 3.20–3.40 (2H, m), 3.61 (4H, t, J=6 Hz), 4.20–4.44 (4H, m), 5.06–5.20 (2H, m), 5.30–5.45 (4H, m)

MS (FAB): 765 (M+H)$^+$

EXAMPLE 26

Synthesis of 2-O-[2-(N-ethyl-N-(2-hydroxyethyl)amino)ethyl]carbamoyl-1,3-O-dioleoylglycerol Using 2-(ethylamino)ethanol, the procedure of Example 25 was otherwise repeated to provide the title compound of the invention.

$^1$H-NMR (200 MHz, CDCl$_3$) δ: 0.88 (6H, t, J=6 Hz), 1.03 (3H, t, 6 Hz), 1.28 (40H, brs.), 1.50–1.70 (4H, m), 1.90–2.10 (8H, m), 2.32 (4H, t, J=8 Hz), 2.54–2.68 (6H, m), 3.20–3.30 (2H, m), 3.56 (2H, t, J=6 Hz), 4.12–4.34 (4H, m), 5.06–5.20 (2H, m), 5.30–5.44 (4H, m)

MS (FAB): 779 (M+H)$^+$

EXAMPLE 27

Synthesis of 2-O-[2-(N,N-di-(2-hydroxyethyl)amino)ethyl]carbamoyl-1,3-O-dioleoylglycerol Using diethanolamine, the procedure of Example 25 was otherwise repeated to provide the title compound of the invention.

$^1$H-NMR (200 MHz, CDCl$_3$) δ: 0.88 (6H, t, J=6 Hz), 1.28 (40H, brs.), 1.50–1.70 (4H, m), 1.90–2.10 (8H, m), 2.32 (4H, t, J=8 Hz), 2.60–2.70 (6H, m), 3.20–3.30 (2H, m), 3.60 (4H, t, J=6 Hz), 4.12–4.40 (4H, m), 5.08–5.20 (1H, m), 5.30–5.42 (4H, m), 5.60–5.70 (1H, brs.)

MS (FAB): 795 (M+H)$^+$

EXAMPLE 28

Synthesis of 2-O-[2-(N-methyl-N-n-butylamino)ethyl]carbamoyl-1,3-O-dioleoylglycerol Using N-methylbutylamine, the procedure of Example 25 was otherwise repeated to provide the title compound of the invention.

$^1$H-NMR (200 MHz, CDCl$_3$) δ: 0.82–0.96 (9H, m), 1.10–1.50 (42H, m), 1.50–1.75 (6H, m), 1.90–2.10 (8H, m), 2.19 (3H, s), 2.26–2.40 (6H, m), 2.46 (2H, m), 3.20–3.30 (2H, m), 4.10–4.30 (4H, m), 5.08–5.20 (1H, m), 5.25–5.40 (4H, m)

MS (FAB): 777 (M+H)$^+$

EXAMPLE 29

Synthesis of 2-O-[2-(4-(2-hydroxyethyl)piperazino)ethyl]carbamoyl-1,3-O-dioleoylglycerol Using 1-(2-hydroxyethyl)piperazine, the procedure of Example 25 was otherwise repeated to provide the title compound of the invention.

$^1$H-NMR (200 MHz, CDCl$_3$) δ: 0.88 (3H, t, J=6 Hz), 1.28 (40H, brs.), 1.50–1.70 (4H, m), 1.90–2.10 (8H, m), 2.32 (4H, t, J=8 Hz), 2.40–2.60 (12H, m), 3.18–3.32 (2H, m), 3.62 (2H, t, J=6 Hz), 4.12–4.32 (4H, m), 5.08–5.24 (2H, m), 5.30–5.40 (4H, m)

MS (FAB): 820 (M+H)$^+$

EXAMPLE 30

Synthesis of 2-O-[2-(N,N,N',N'-tetramethylguanidino) ethyl]carbamoyl-1,3-O-dioleoylglycerol Using N,N,N',N'-tetramethylguanidine, the procedure of Example 25 was otherwise repeated to provide the title compound of the invention.

$^1$H-NMR (200 MHz, CDCl$_3$) δ: 0.88 (3H, t, J=6 Hz), 1.27 (40H, brs.), 1.50–1.70 (4H, m), 1.90–2.10 (8H, m), 2.30 (4H, t, J=8 Hz), 2.96 (3H, s), 3.10 (3H, s), 3.35–3.40 (2H, m), 3.60–3.70 (2H, m), 4.04–4.34 (4H, m), 4.98–5.08 (1H, m), 5.30–5.40 (4H, m), 6.30–6.40 (1H, m)

MS (FAB): 805 (M+H)$^+$

EXAMPLE 31

Synthesis of 2-O-[2-(N-(2-diethylamino)ethyl-N-methylamino)ethyl]carbamoyl-1,3-O-dioleoylglycerol Using N,N-diethyl-N'-methylethylenediamine, the procedure of Example 25 was otherwise repeated to provide the title compound of the invention.

$^1$H-NMR (200 MHz, CDCl$_3$) δ: 0.88 (6H, t, J=6 Hz), 1.04 (6H, t, J=6 Hz), 1.26 (40H, brs.), 1.50–1.70 (4H, m), 1.90–2.10 (8H, m), 2.26–2.36 (7H, m), 2.44–2.64 (10H, m), 3.15–3.25 (2H, m), 4.16–4.26 (4H, m), 5.08–5.18 (1H, m), 5.30–5.40 (4H, m), 6.46–6.60 (1H, brs.)

MS (FAB): 820 (M+H)$^+$

EXAMPLE 32

Synthesis of 2-O-[2-(4-ethylpiperazino)ethyl] carbamoyl-1,3-O-dioleoylglycerol

Using 1-ethylpiperazine, the procedure of Example 25 was otherwise repeated to provide the title compound of the invention.

$^1$H-NMR (200 MHz, CDCl$_3$) δ: 0.88 (6H, t, J=6 Hz), 1.10 (3H, t, J=6 Hz), 1.26 (40H, brs.), 1.50–1.70 (4H, m), 1.90–2.10 (8H, m), 2.32 (4H, t, J=8 Hz), 2.38–2.60 (12H, m), 3.22–3.34 (2H, m), 4.12–4.34 (4H, m), 5.10–5.30 (2H, m), 5.30–5.42 (4H, m)

MS (FAB): 802 (M+H)$^+$

EXAMPLE 33

Synthesis of 2-O-[2-(N-ethyl-N-methylamino)ethyl] carbamoyl-1,3-O-dioleoylglycerol In 3 ml of chloroform was dissolved 131 mg (0.170 mmol) of 1,3-O-dioleoyl-2-O-(2-bromoethyl) carbamoylglycerol followed by addition of 470 mg (7.951 mmol) of N-ethylmethylamine and the reaction was conducted in a sealed tube at 80° C. overnight. This reaction mixture was then washed with 5% sodium dihydrogen phosphate-H$_2$O, dried and concentrated. The residue was subjected to column chromatography silica gel/methylene chloride-methanol) to provide 104 mg (81.5%) of the title compound of the invention.

$^1$H-NMR (200MHz, CDCl$_3$) δ: 0.88 (6H, t, J=6 Hz), 1.04 (3H, t, J=6 Hz), 1.26 (40H, brs.), 1.50–1.70 (4H, m), 1.90–2.10 (8H, m), 2.20 (3H, s), 2.32 (4H, t, J=8 Hz), 2.38–2.52 (4H, m), 3.20–3.30 (2H, m), 4.12–4.32 (4H, m), 5.10–5.20 (1H, m), 5.25–5.42 (5H, m)

MS (FAB): 749 (M+H)$^+$

EXAMPLE 34

Synthesis of 2-O-(2-diethylaminoethyl)carbamoyl-1, 3-O-dipalmitoylglycerol

Using 1,3-O-dipalmitoylglycerol and N,N-diethylethylenediamine, the procedure of Example 13 was otherwise repeated to provide the title compound of the invention.

$^1$H-NMR (200 MHz, CDCl$_3$) δ: 0.87 (6H, t, J=6 Hz), 1.00 (6H, t, J=6 Hz), 1.25 (48H, brs.), 1.50–1.70 (4H, m), 2.30 (4H, t, J=8 Hz), 2.46–2.60 (6H, m), 3.10–3.30 (2H, m), 4.12–4.32 (4H, m), 5.10–5.20 (1H, m), 5.20–5.35 (1H, m)

MS (FAB): 711 (M+H)$^+$

EXAMPLE 35

Synthesis of 2-diethylaminoethyl N-(1,3-dioleoyloxypropan-2-yl)carbamate

In methylene chloride was dissolved 470 mg (4 mmol) of 2-diethylaminoethanol. After addition of 633 mg (8 mmol) of pyridine, 690 mg (4.4 mmol) of phenyl chloroformate was further added under ice-cooling and the reaction was conducted at ambient temperature for 2 hours. After completion of the reaction, the solvent was distilled off and the residue was transferred into ethyl acetate-1% aqueous sodium hydrogen carbonate solution. The ethyl acetate layer was separated, dried over sodium sulfate, and concentrated under reduced pressure to give 705 mg (74%) of crude carbonate compound. This crude carbonate was dissolved in anhydrous pyridine followed by addition of 134 mg (1.47 mmol) of 2-amino-1,3-propanediol and the reaction was carried out at 80° C. overnight. Then, 973 mg (3.2 mmol) of oleoyl chloride was added and the reaction was further conducted at ambient temperature for 24 hours. After completion of the reaction, the solvent was distilled off under reduced pressure and the residue was transferred into methylene chloride-saturated aqueous sodium hydrogen carbonate solution and dried over sodium sulfate. The solvent was then removed under reduced pressure and the residue was subjected to column chromatography (silica gel/methylene chloride-methanol) to provide 250 mg (22%) of the title compound of the invention.

$^1$H-NMR (200 MHz, CDCl$_3$) δ: 0.87 (6H, t, J=6 Hz), 1.04 (6H, t, J=6 Hz), 1.28 (40H, brs.), 1.50–1.70 (4H, m), 1.90–2.10 (8H, m), 2.30 (4H, t, J=8 Hz), 2.50–2.70 (6H, m), 4.00–4.30 (7H, m), 5.05–5.20 (1H, m), 5.25–5.45 (4H, m)

MS (FAB): 763 (M+H)$^+$

EXAMPLE 36

Synthesis of 2-O-(3-diethylaminopropionyl)-1,3-O-dioleoylglycerol

In a solvent mixture of 3 ml N,N-dimethylformamide and 6 ml methylene chloride was dissolved 172 mg (0.277 mmol) of 1,3-dioleoylglycerol followed by addition of 101 mg (0.556 mmol) of N,N-diethyl-β-alanine (hydrochloride), 114 mg (0.553 mmol) of N,N-dicyclohexylcarbodiimide, and 7 mg (0.057 mmol) of 4-dimethylaminopyridine and the mixture was stirred overnight. This reaction mixture was then filtered and the filtrate was concentrated under reduced pressure. The residue was dissolved in methylene chloride and washed with water. The washed solution was dried and concentrated and the residue was subjected to column chromatography (silica gel/methylene chloride-methanol) to provide 129 mg (62%) of the title compound of the invention.

$^1$ H-NMR (200 MHz, CDCl$_3$) δ: 0.88 (6H, t, J=6 Hz), 1.20–1.40 (46H, m), 1.50–1.70 (4H, m), 1.90–2.10 (8H, m), 2.32 (4H, t, J=8 Hz), 2.76–2.84 (6H, m), 3.04–3.14 (2H, m), 4.08–4.42 (4H, m), 5.18–5.30 (1H, m), 5.30–5.44 (4H, m)

MS (FAB): 748 (M+H)$^+$

EXAMPLE 37

Synthesis of O-(2-dimethylaminoethyl),O'-(1,3-dioleoyloxypropyl)methylphosphonate To 310 mg (0.50 mmol) of 1,3-dioleoylglycerol dried by azeotropic distillation with pyridine was added 9.1 ml (1 mmol) of 0.11 M methyl bis-O,O-(1-benzotriazolyl) phosphonate-dioxane and the reaction was conducted at ambient temperature for 3 hours. To this reaction mixture were added 446 mg (5 mmol) of 2-dimethylaminoethanol and 411 mg (5 mmol) of 1-methylimidazole and the reaction was further conducted at ambient temperature overnight. The reaction mixture was then treated with methylene chloride-5% sodium dihydrogen phosphate solution and the methylene chloride layer was dried over sodium sulfate and concentrated under reduced pressure. The residue was subjected to column chromatography (silica gel/methylene chloride-methanol) to provide 272 mg (59%) of the title compound of the invention.

$^1$H-NMR (200 MHz, CDCl$_3$) δ: 0.86 (6H, t, J=6 Hz), 1.25 (40H, brs), 1.54 (3H, d, J=20 Hz), 1.50–1.70 (4H, m), 2.32 (4H, t, J=8 Hz), 2.35 (6H, s), 2.68 (2H, t, J=6 Hz), 4.05-4.25 (4H, m), 4.25–4.35 (2H, m), 4.70–4.90 (1H, m), 5.25–5.40 (4H, m)

MS (FAB): 770 (M+H)$^+$

EXAMPLE 38

Synthesis of O-(2-aminoethyl)-O'-(1,3-dioleoyloxypropyl)methylphosphonate

Using t-butyl N-(2-hydroxyethyl)carbamate in lieu of 2-dimethylaminoethanol, the procedure of Example 37 was otherwise repeated and the resulting compound was treated with trifluoroacetic acid/methylene chloride (1:2) to provide the title compound of the invention.

$^1$H-NMR (200 MHz, CDCl$_3$) δ: 0.88 (6H, t, J=6 Hz), 2.25 (40H, brs), 1.50–1.90 (7H, m), 1.90–2.10 (8H, m), 2.34 (4H, t, J=8 Hz), 3.30–3.40 (2H, s), 4.10–4.50 (6H, m), 4.75–4.90 (1H, m), 5.30–5.40 (4H, m)

MS (FAB): 742 (M+H)$^+$

EXAMPLE 39

Synthesis of O-(2-diethylaminoethyl)-O'-(1,3-dioleoyloxypropyl)methylphosphonate Using 2-diethylaminoethanol, the procedure of Example 37 was otherwise repeated to provide 166 mg (70.7%) of the title compound of the invention.

$^1$H-NMR (200 MHz, CDCl$_3$) δ: 0.87 (6H, t, J=6 Hz), 1.01 (6H, t, J=6 Hz), 1.26 (40H, brs), 1.48–1.70 (7H, m), 1.90–2.10 (8H, m), 2.32 (4H, t, J=8 Hz), 2.57 (4H, q, J=6 Hz), 2.80 (2H, t, J=6 Hz), 3.90–4.40 (6H, m), 4.70–4.90 (1H, m), 5.30–5.42 (4H, m)

MS (FAB): 798 (M+H)$^+$

EXAMPLE 40

In 200 μl of chloroform, in a vial, were dissolved 5 mg of the compound of the invention according to Example 4 and 5 mg of egg yolk phosphatidylethanolamine. Then, nitrogen gas was blasted against the solution to remove the chloroform, leaving a thin film on the internal wall of the vial. The vial was then allowed to stand overnight under reduced pressure and after addition of 2 ml of sterile distilled water, was agitated in a vortex mixer to exfoliate the film. After purging with nitrogen gas, the vial was hermetically stoppered and allowed to stand at 4° C. for 3 hours. Then, sonication was carried out for 10 minutes with a bath sonicator to provide a lipid device of the invention.

EXAMPLE 41

Using the compound of the invention according to Example 7, a lipid device of the invention was prepared in otherwise the same manner as Example 40.

EXAMPLE 42

Using the compound of the invention according to Example 20, a lipid device of the invention was prepared in otherwise the same manner as Example 40.

EXAMPLE 43

Using egg yolk phosphatidylcholine in lieu of egg yolk phosphatidylethanolamine, the procedure of Example 40 was repeated to provide a device of the invention.

EXAMPLE 44

Using the compound of the invention according to Example 7, a lipid device of the invention was prepared in otherwise the same manner as Example 43.

EXAMPLE 45

Using the compound of the invention according to Example 20, a lipid device of the invention was prepared in otherwise the same manner as Example 43.

EXAMPLE 46

Injectable Composition

To 60 μl of the device of the invention according to Example 40 was added 0.9 ml of physiological saline solution. To this mixture was added 0.1 ml of a 100 μg/ml saline solution of a mismatched double-stranded RNA [a double-stranded RNA consisting of a polyinosinic acid and a cytidylic acid copolymer containing one unit of 4-thiouridylic acid substituted per 20 cytidylic acid units, with the overall molecular size distribution being controlled to about 50–10,000 bases] (hereinafter referred to as the investigational drug) and the mixture was agitated to provide an injectable composition.

EXAMPLE 47

Injectable Composition

Using the devices of the invention according to Examples 41–45, injectable compositions were prepared in otherwise the same manner as Example 46.

EXAMPLE 48

Injectable Composition

Using 10 mM phosphate buffer in lieu of physiological saline, the procedure of Example 46 was otherwise repeated to provide an injectable composition.

Test Example 1

Hemolytic Action

To 0.9 ml of a rat erythrocyte suspension washed with an isotonic solution was added 0.1 ml of an aqueous suspension of the compound of the invention and the mixture was incubated at 37° C. with agitation for 45 minutes. This mixture was centrifuged at 3000 rpm for 2 minutes and the absorbance of the supernatant was measured at 540 nm. With the absorbance of the sample obtained with addition of 0.1 ml of the isotonic solution being taken as 0% (no hemolysis) and the absorbance of the sample obtained with addition of 0.1 ml of 0.1% Triton X-100 being taken as 100% (complete hemolysis), the degree of hemolysis for the device of the invention was calculated. The results are shown in Table 1. The erythrocyte suspension was so prepared that the absorbance at 540 nm after complete hemolysis would be 1.2.

TABLE 1

| Concn. of lipid (μg/ml) | DOTMA | Exp. 1 | Exp. 12 | Exp. 13 | Exp. 15 | Exp. 16 |
|---|---|---|---|---|---|---|
| 0.3 | 4.9 | 4.7 | 4.4 | 4.4 | 7 | 5.1 |
| 1 | 8.4 | 5.8 | 5.3 | 6 | 10.6 | 7.3 |
| 3 | 28.3 | 7 | 6.2 | 8 | 16.6 | 10.4 |
| 10 | 58.8 | 13.7 | 12.6 | 14.6 | 21.6 | 16.8 |

TABLE 1-continued

| Concn. of lipid (μg/ml) | DOTMA | Exp. 1 | Exp. 12 | Exp. 13 | Exp. 15 | Exp. 16 |
|---|---|---|---|---|---|---|
| 30 | 89.5 | 35 | 31.6 | 31.5 | 87.2 | 32.8 |
| *H (30%) | 3 | 25 | 30 | 30 | 13 | 30 |

Exp. = Example hemolysis rate (%)
*H (30%) stands for the concentration of the lipid that causes hemolysis in 30% of erythrocytes.

It is apparent from Table 1 that compared with the commercial lipid device, the hemolytic action of the device of the invention that causes hemolysis in 30% of erythrocytes is approximately 1/10. It was, therefore, suggested that the device of the invention is a device of very low toxicity.
Test Example 2 HeLaS3 cell growth inhibitory action (in vitro)

A 96-well plate was seeded with HeLaS3 cells at a cell density of $10^4$ cells/well (90 μl). On the following day, 10 μl/well of Lipofectin (trademark) or the device of the invention, each having a lipid concentration of 30 μg/ml and containing a varying concentration of the investigational drug, was added. The plate was incubated for 72 hours after addition and, then, 10 μl per well of a 5 mg/ml solution of MTT (3-(4,5-dimethylthiazol-2-yl)-2,5-diphenyltetrazolium bromide was added. After 2–4 hours, the reaction was stopped by adding isopropyl alcohol/0.04N hydrochloric acid mixture. After suspension of each well, the absorbance at 540 nm was measured with a plate reader (manufactured by Corona) and the HeLaS3 cell growth inhibition rate (%) was calculated. This calculation was performed according to the equation given below. The cell growth inhibition rate of the investigational drug accompanying neither Lipofectin nor the device of the invention was used as control.

TABLE 2

$$\% \text{ Inhibition} = \left(1 - \frac{\text{Cell count in presence of the investigational drug}}{\text{Cell count in presence of saline}}\right) \times 100$$

The results are shown in Table 2

| | Control | Lipofectine ® | Exp. 1 + EPE | Exp. 2 + EPE |
|---|---|---|---|---|
| Concn of the investigational drug (μg/ml) | | | | |
| 0 | 0 | 0 | 0 | 8 | 0 |
| 0.001 | 0 | — | — | — |
| 0.01 | 0 | 25 | 59 | 21 |
| 0.1 | 0 | 76 | 85 | 92 |
| 1 | 0 | 100 | 95 | 96 |
| 10 | 0 | 100 | 92 | 94 |
| IC$_{50}$ | | 0.03 | 0.01 | 0.03 |

| Exp. 4 | | Exp. 7 | | Exp. 9 |
|---|---|---|---|---|
| + EPE | + ELC | + EPE | + ELC | + EPE |
| 3 | 0 | 1 | 6 | 7 |
| 22 | 0 | 28 | 8 | 58 |
| 85 | 63 | 85 | 50 | 93 |
| 100 | 92 | 100 | 91 | 100 |

TABLE 2-continued $$\% \text{ Inhibition} = \left(1 - \frac{\text{Cell count in presence of the investigational drug}}{\text{Cell count in presence of saline}}\right) \times 100$$

The results are shown in Table 2

| 93 | 96 | 69 | 99 | 95 |
|---|---|---|---|---|
| — | — | — | — | — |
| 0.003 | 0.006 | 0.002 | 0.01 | 0.001 |

| Exp. 9 + ELC | Exp. 12 + EPE | Exp. 13 + EPE | Exp. 15 + EPE | Exp. 16 + EPE |
|---|---|---|---|---|
| 0 | 0 | 0 | 0 | 0 |
| 44 | — | — | — | — |
| 44 | 64 | 51 | 75 | 80 |
| 74 | 94 | 88 | 86 | 93 |
| 77 | 95 | 98 | 83 | 100 |
| — | 98 | 100 | 80 | 100 |
| 0.03 | 0.006 | 0.01 | 0.005 | 0.004 |

| Exp. 18 | | Exp. 19 | Exp. 20 | |
|---|---|---|---|---|
| + EPE | + ELC | + EPE | + EPE | + ELC |
| 6 | 3 | 0 | 0 | 0 |
| 34 | 14 | 68 | 50 | 2 |
| 97 | 39 | 100 | 95 | 81 |
| 100 | 59 | 100 | 100 | 100 |
| 100 | 59 | 100 | 100 | 97 |
| — | — | — | — | — |
| 0.04 | 0.08 | 0.0006 | 0.001 | 0.004 |

| Exp. 24 | Exp. 26 | | Exp. 28 | Exp. 33 |
|---|---|---|---|---|
| + EPE | + EPE | + ELC | + EPE | + EPE |
| 0 | 0 | 3 | 0 | 1 |
| 6 | 59 | 28 | 0 | 49 |
| 70 | 94 | 66 | 23 | 95 |
| 100 | 100 | 76 | 80 | 100 |
| 77 | 100 | 85 | 80 | 89 |
| — | — | — | — | — |
| 0.005 | 0.001 | 0.004 | 0.03 | 0.001 |

| Exp. 33 + ELC | Exp. 34 + EPE |
|---|---|
| 0 | 0 |
| 20 | 25 |
| 92 | 95 |
| 100 | 100 |
| 100 | 100 |
| — | — |
| 0.004 | 0.003 |

Exp. = Example
The values in Table represent inhibition rate (%).
EPE; egg yolk phosphatidylethanolamine
ELC; egg yolk phosphatidylcholine It is apparent from Table 2 that the growth inhibitory effect obtained with the device of the invention was 1 through 3~20-fold as high as the effect obtained with the conventional lipid device Lipofectin (trademark).

However, a lipid device consisting of 3 β- [N-(N',N'-dimethylaminoethane)-carbamoyl]cholesterol (DC-chol) and egg yolk phosphatridylethanolamine (1:1) was prepared according to the literature [Biochemical and Biophysical Research Communication, 280–285, Vol. 179 No. 1 (1991)] and compared with the devices of the invention (Examples 40 and 43) for HeLaS3 cell growth inhibitory activity. It was found that when 0.1 μg/ml of the investigational device was applied at the lipid concentration of 30 μg/ml, the devices of the invention were about 6-fold as effective as the DC-chol lipid device in cell growth inhibitory activity.

What is claimed is:

1. A compound of the following general formula [I]:

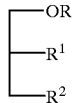
(I)

wherein $R^1$ and $R^2$ are not the same and each represents OY or —A—$(CH_2)_n$—E, n represents a whole number of 1–4, E represents

(where $R^3$ and $R^4$ are the same or different and each represents hydrogen, lower($C_{1-4}$)alkyl, hydroxy-lower($C_{1-4}$)alkyl, or mono- or di-(lower)alkylaminoalkyl($C_{2-8}$)), A represents the following ①, ②, ④, ⑥ or ⑦.

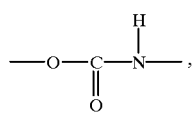 ①

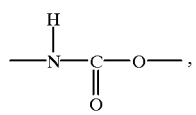 ②

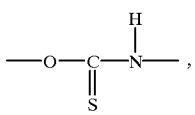 ④

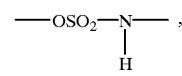 ⑥

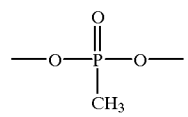 ⑦

R and Y are the same or different and each represents a saturated or unsaturated aliphatic hydrocarbon group of 10–30 carbon atoms or a saturated or unsaturated fatty acid residue of 10–30 carbon atoms.

2. A compound of the following general formula [I'],

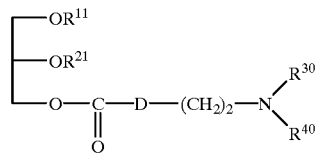
(I')

wherein $R^{11}$ and $R^{21}$ are the same or different and each represents oley 1 or oleoyl, D represents —NH—, $R^{30}$ and $R^{40}$ are the same or different and each represents methyl or ethyl.

3. A compound according to claim 1 which is selected from the group consisting of 3-O-(2-dimethylaminoethyl) carbamoyl-1,2-O-dioleylglycerol, 3-O-(2-diethylaminoethyl)carbamoyl-1,2-O-dioleylglycerol and 2-O-(2-diethylaminoethyl)carbamoyl-1,3-O-dioleoylglycerol.

4. A DDS device characterized by comprising a compound of general formula

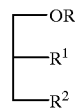

and a phospholipid as essential components.

5. A DDS device characterized by comprising a compound of general formula

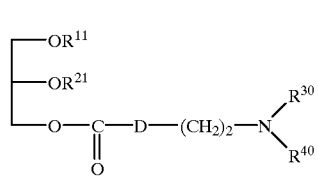

and a phospholipid as essential components.

6. A DDS device characterized by comprising a compound selected from the group consisting of 3-O-(2-dimethylaminoethyl)carbamoyl-1,2-O-dioleylglycerol, 3-O-(2-diethylaminoethyl)carbamoyl-1,2-O-dioleyl glycerol and 2-O-(2-diethylaminoethyl)carbamoyl-1,3-O-dioleoylglycerol, and a phospholipid as essential components.

7. A DDS device according to claim 4 wherein said phospholipid is phosphatidylethanolamine or phosphatidylcholine.

8. A DDS device according to claim 5 wherein said phospholipid is phosphatidylethanolamine or phosphatidylcholine.

9. A DDS device according to claim 6 wherein said phospholipid is phosphatidylethanolamine or phosphatidylcholine.

10. A pharmaceutical composition characterized by comprising the DDS device claimed in claim 4, 5, 6, 7, 8 or claim 9 and a physiologically active substance.

11. A pharmaceutical composition characterized by comprising the DDS device claimed in claims 4, 6, 8, 5, 7 or 9, and a physiologically active substance and wherein said physiologically active substance is a double-stranded RNA.

12. A pharmaceutical composition characterized by comprising the DDS device claimed in claims 4, 6, 8, 5, or 9, and a physiologically active substance and wherein said physiologically active substance is a double-stranded RNA consisting of a polyinosinic acid and a cytidylic acid copolymer containing one unit of 4-thiouridylic acid substituted for every 20 units of cytidylic acid, the overall molecular size distribution of which is controlled within the range of about 50–10,000 bases.

* * * * *